US007932212B2

(12) United States Patent
Taylor et al.

(10) Patent No.: US 7,932,212 B2
(45) Date of Patent: Apr. 26, 2011

(54) INHIBITION OF PLACENTA GROWTH FACTOR (PLGF) MEDIATED METASTASIS AND/OR ANGIOGENESIS

(75) Inventors: Alice P. Taylor, Alpharetta, GA (US); David M. Goldenberg, Mendham, NJ (US); Chien-Hsing Chang, Downingtown, PA (US)

(73) Assignees: Center for Molecular Medicine & Immunology, Belleville, NJ (US); Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 12/620,013

(22) Filed: Nov. 17, 2009

(65) Prior Publication Data

US 2010/0216662 A1 Aug. 26, 2010

Related U.S. Application Data

(62) Division of application No. 11/581,287, filed on Oct. 16, 2006, now Pat. No. 7,642,239.

(60) Provisional application No. 60/728,292, filed on Oct. 19, 2005.

(51) Int. Cl.
*C40B 30/04* (2006.01)

(52) U.S. Cl. .......................................................... 506/9

(58) Field of Classification Search ........................ None
See application file for complete search history.

(56) References Cited

U.S. PATENT DOCUMENTS 5,698,178 A 12/1997 Goldenberg et al.
5,874,540 A 2/1999 Hansen et al.
6,342,221 B1 1/2002 Thorpe et al.
6,930,089 B2 8/2005 Carmeliet
7,105,168 B1 9/2006 Carmeliet et al.
7,226,908 B2 6/2007 Carmeliet et al.
7,307,060 B2 12/2007 Compernolle et al.
7,357,929 B2 4/2008 Carmeliet et al.
7,482,004 B2 * 1/2009 Carmeliet et al. ......... 424/145.1
2003/0180286 A1 9/2003 Carmeliet et al.
2007/0027100 A1 2/2007 Carmeliet et al.
2007/0172423 A1 7/2007 Li et al.
2007/0249539 A1 10/2007 Carmeliet et al.

FOREIGN PATENT DOCUMENTS

WO 99/24056 5/1999
WO 0185796 11/2001
WO WO 02/46213 * 6/2002

OTHER PUBLICATIONS

Ahmad et al., "Elevated Placental Soluble Vascular Endothelial Growth Factor Receptor-1 Inhibits Angiogenesis in Preeclampsia", Circ. Res. 95:884-891 (2004).

Hornig et al., "Release and complex formation of soluble VEGFR-1 from endothelial cells and biological fluids", Lab. Invest. 80(4):443-54 (2000).

Supplemental European Search Report for 06826058.7, filed Jun. 16, 2006, date of mailing Oct. 7, 2009.

Donnini et al., "Expression and Localization of Placenta Growth Factor and PlGF Receptors in Human Meningiomas", J. Pathol. 189:66-71 (1999).

Fischer et al., "Anti-PlGF Inhibits Growth of VEGF(R)-Inhibitor-Resistant Tumors without Affecting Healthy Vessels", Cell 131:463-475 (2007).

Selvaraj et al., "Mechanism of Monocyte Activation and Expression of Proinflammatory Cytochemokines by Placenta Growth Factor", Blood 2003, vol. 102, No. 4, pp. 1515-1524.

Semenza, Gregg L., "A new Weapon for Attacking Tumor Blood Vessels", N. Engl. J. Med. May 8, 2008;358 (19):2066-7.

* cited by examiner

*Primary Examiner* — Laura B Goddard
(74) *Attorney, Agent, or Firm* — Richard A. Nakashima

(57) ABSTRACT

The present invention concerns methods and compositions for inhibiting angiogenesis and/or tumor growth, survival and/or metastasis. In particular embodiments, the methods and compositions may concern ligands against placenta growth factor (PlGF), such as BP-1, BP-2, BP-3 or BP-4. Some methods may comprise administering one or more PlGF ligands, alone or in combination with one or more other agents, such as chemotherapeutic agents, other anti-angiogenic agents, immunotherapeutic agents or radioimmunotherapeutic agents to a subject. The PlGF ligands are effective to inhibit angiogenesis, tumor cell motility, tumor metastasis, tumor growth and/or tumor survival. In certain embodiments, PlGF ligands may be administered to subjects to ameliorate other angiogenesis related conditions, such as macular degeneration. In some embodiments, PlGF expression levels may be determined by any known method to select those patients most likely to respond to PlGF targeted therapies.

13 Claims, 6 Drawing Sheets

A490
0.5
0.4
0.3
0.2
0.1
0.0
A
B
C
D
*
First reagent
1 μM BP1
2.5/25 U/ml heparin
Second reagent
1 μM BP1
2.5 U/ml heparin
+

Invading cells
0
10
20
30
40
50
60
UT
2 nM PlGF
2 nM VEGF
Pl+BP1
Pl+CPA
VE+BP1
VE+CPA
0.2 nM PlGFA
0.2 nM VEGF
*
*

MDA-MB-231

INHIBITION OF PLACENTA GROWTH FACTOR (PLGF) MEDIATED METASTASIS AND/OR ANGIOGENESIS

RELATED APPLICATIONS

The present application is a divisional of U.S. patent application Ser. No. 11/581,287, filed Oct. 16, 2006, now U.S. Pat. No. 7,642,239 which claims the benefit under 35 U.S.C. §119(e) of provisional U.S. Patent Application Ser. No. 60/728,292, filed on Oct. 19, 2005, the entire text of which is incorporated herein by reference.

FEDERALLY FUNDED RESEARCH

The studies disclosed herein were supported in part by grant DAMD 17-03-1-0758 from the U.S. Department of Defense (A.P.T.). The U.S. government may have certain rights to practice the subject invention.

BACKGROUND

1. Field of the Invention

The present invention concerns methods and compositions for inhibiting angiogenesis, particularly pathologic angiogenesis and/or growth and metastasis of tumors. In particular embodiments, the compositions and methods concern inhibitors targeted to placenta growth factor-2 (PlGF) and/or its receptor, Flt-1, including but not limited to peptides, antibodies, antibody fragments, humanized antibodies, chimeric antibodies, antibody analogs, aptamers, organic compounds and/or any other molecule or compound known in the art that may be used to inhibit PlGF-mediated angiogenesis and/or metastasis. In more particular embodiments, the inhibitors may be peptides isolated by phage display against PlGF.

2. Description of Related Art

The high expression of angiogenic growth factors is necessary for the growth and development of diverse cancers (Cao et al., 1998*, J Clin Invest* 101:1055-1063). Among such angiogenic growth factors, high expression of vascular endothelial growth factor (VEGF) has received the most attention with regard to being associated with increased malignancy and metastasis (Abdulrauf et al., 1998*, J Neurosurg* 88:513-52; Ahmed et al., 2000, Placenta 21 Suppl A, S16-24). However, the role of VEGF and other members of the VEGF family of growth factors in tumor recurrence or metastatic growth has not been clearly established. Many treatments, including radiation, cytokines, and cytotoxic agents, owe some of their therapeutic activity to anti-angiogenic mechanisms, one of which is the down-regulation of VEGF (Taylor et al., 2002a, *Clin Cancer Res* 8:1213-1222; Jiang et al., 1999*, Mol Carcinog* 26:213-225; Machein et al., 1999*, Neuropathol Appl Neurobiol* 25:104-112). Yet, marked inhibition of VEGF does not always result in durable responses or even cure. This suggests that factors other than VEGF may be capable of restoring a blood supply to surviving tumor cells.

A need exists in the field for methods and compositions directed towards the effective inhibition of tumor angiogenesis and/or growth and metastasis, as well as angiogenesis associated with other diseases.

SUMMARY OF THE INVENTION

The present invention fulfills an unresolved need in the art by providing methods and compositions for inhibiting, suppressing, blocking and/or eliminating angiogenesis and/or tumor metastasis. In certain embodiments, the compositions and/or methods may concern ligands for placenta growth factor-2 (PlGF), and/or ligands binding to both Flt-1 and PlGF. Such ligands may include, but are not limited to, peptides, antibodies, antibody fragments, humanized antibodies, chimeric antibodies, antibody analogs, aptamers, organic compounds and/or any other molecules or compounds known in the art that are ligands for PlGF.

In various embodiments, the PlGF ligands may be peptides. Methods for identifying peptides that bind to particular targets are well known in the art, including for example phage display techniques as discussed below. In phage display, libraries of peptides expressed on the surface of phage, such as filamentous bacteriophage, are created and may be screened by selection against the target(s) of interest. After one or more rounds of screening (panning) against the target, phage containing display peptides that bind to the target may be isolated and the peptide sequences determined, for example by sequencing of the peptide-encoding DNA inserts in the phage nucleic acid.

Other embodiments concern methods and/or compositions for treating subjects, such as subjects with cancer and/or with a condition related to angiogenesis (e.g., macular degeneration, etc.). Subjects may include, but are not limited to, humans, animals, cats, dogs, cows, sheep, goats, horses, alpacas and mammals. The methods and compositions may comprise one or more PlGF ligands to be administered to a subject. In preferred embodiments, peptides identified as ligands by phage display against PlGF may be administered. Administration may be by any route known in the art, such as oral, nasal, buccal, inhalational, rectal, vaginal or topical. Alternatively, administration may be by orthotopic, intradermal, subcutaneous, intramuscular, intraperitoneal, intraarterial, intrathecal or intravenous injection. In preferred embodiments, the PlGF ligand (inhibitor) is orally administered. In more preferred embodiments, the PlGF ligand may comprise the sequence of (binding protein) BP-1, BP-2, BP-3 or BP-4, as disclosed in the Examples below.

The administration of PlGF ligands may be effective to inhibit or eliminate tumor metastasis, angiogenesis in solid tumors, tumor cell survival and/or tumor cell mobility. In preferred embodiments, administration of one or more PlGF ligands may prevent tumors from metastasizing or may result in regression or growth inhibition of existing tumors. The skilled artisan will realize that one or more PlGF ligands may be administered alone or alternatively in conjunction with other known therapeutic treatments for cancer and/or angiogenesis, such as chemotherapy, radiation therapy, immunotherapy, anti-VEGF agents and/or other known anti-angiogenesis agents and the like. In some embodiments, the PlGF ligands may be administered with a bispecific antibody, with one binding site for the PlGF ligand and a second binding site for a tumor antigen or other target. In other embodiments, PlGF ligands may be covalently attached to or provided as a fusion protein with an antibody, antibody fragment, monoclonal antibody, Fc fragment, Fc-binding protein or antibody binding protein.

In alternative embodiments, PlGF ligands may be of use to treat angiogenesis related conditions besides cancer. Examples of conditions related to angiogenesis include, but are not limited to, rheumatoid arthritis, inflammatory bowel disease, Crohn's disease, ulcerative colitis, sarcoidosis, asthma, edema, pulmonary hypertension, formation and development of tumors, psoriasis, diabetic retinopathy, macular degeneration, corneal graft rejection, neovascular glaucoma, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis and wound granulation.

In other alternative embodiments, the PlGF ligands disclosed herein may be used as targeting peptides, for example by conjugation with a complex or therapeutic agents. PlGF ligands, such as BP-1, BP-2, BP-3 and/or BP-4, may be covalently or non-covalently attached to various moieties by methods well known in the art, such as the use of covalent cross-linking reagents. Many such agents, such as carbodiimides, bisimidates, N-hydroxysuccinimide ester of suberic acid, dimethyl-3,3'-dithio-bispropionimidate, azidoglyoxal, 1,5-difluoro-2,4-(dinitrobenzene) and other cross-linkers of use for proteins and/or peptides are known and may be used. In various embodiments, PlGF ligands may be attached to antibodies, antibody fragments, chemotherapeutic agents, anti-angiogenic agents, pro-apoptosis agents, liposomes incorporating such agents or any other known therapeutic compound.

In still other embodiments, the PlGF ligands may be used as adjuncts for diagnosis and/or imaging purposes. For example, PlGF ligands may be tagged with any known contrast or detection agent or may be detected using any known methodologies, such as ELISA, etc. The PlGF ligands may be used ex vivo, for example by immunohistochemistry of tissue sections, to detect tumors or other tissues that express PlGF. Alternatively, PlGF ligands may be administered to a subject for in vivo detection of tissues expressing PlGF. Such compositions and methods may be of use, for example, to detect or diagnose the presence of a PlGF-expressing tumor and/or to identify those subjects with an angiogenesis or cell motility-related condition that might benefit from therapies targeted against PlGF.

BRIEF DESCRIPTION OF THE DRAWINGS

The following drawings form part of the present specification and are included to further demonstrate certain aspects of particular embodiments of the invention. The embodiments may be better understood by reference to one or more of these drawings in combination with the detailed description presented herein.

FIG. 4A—MCF-7 human breast cancer cells. FIG. 4B—MDA-MB-468 human breast cancer cells. FIG. 4C—MDA-MB-231 human breast cancer cells.

FIG. 5A—tumors treated with binding peptide 1. FIG. 5B—tumors treated with binding peptide 3.

DESCRIPTION OF ILLUSTRATIVE EMBODIMENTS

Figure 1:
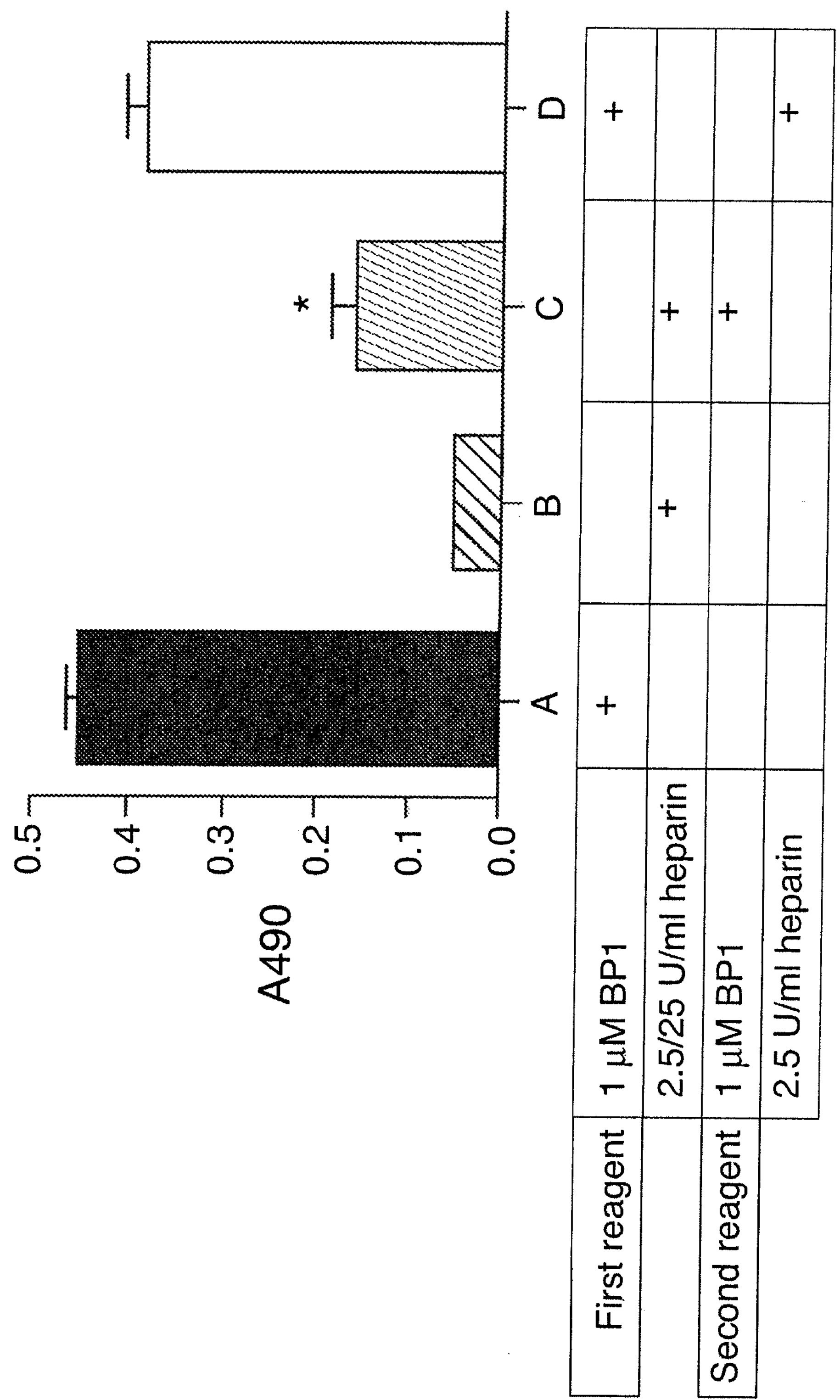
FIG. 1. BP1 interacts with the heparin-binding region of Flt-1. Reagents were added to Flt-1-coated wells as indicated in the lower part of the Figure. BP1 used in this experiment contains a linker and the FLAG epitope at its C-terminus. Peptide binding was assessed by probing for the FLAG epitope. A: 1 μM BP1 only; B: 2.5/25 U/ml heparin only; C, 2.5 U/ml heparin followed by 1 μM BP1; D: 1 μM BP1 followed by 2.5 U/ml heparin. Values shown are mean of duplicate wells±SD from 2 separate experiments. * $P<0.0002$ for heparin followed by 1 μM BP1 (C) vs. BP1 only (A) (ANOVA).

All documents, or portions of documents, cited in this application, including but not limited to patents, patent applications, articles, books, and treatises, are hereby expressly incorporated by reference in their entirety.

DEFINITIONS

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

A "ligand" refers to any molecule, compound or composition that is capable of binding to a target. For example, a PlGF ligand is a ligand that can bind to PlGF. Binding capacity may be determined directly by any method known in the art, such as radioassay using labeled ligands or targets, affinity chromatography, immunoprecipitation, dot blot, slot blot, Western blot, ELISA, microarray binding, etc. Alternatively, binding may be determined by indirect methods, such as panning of peptide-bearing phage against a target using a phage display technique.

Abbreviations used are:

BSA, bovine serum albumin;

ELISA, enzyme-linked immunosorbent assay;

FGF, fibroblast growth factor;

FGFR, fibroblast growth factor receptor;

FITC, fluorescein iso-thiocyanate;

flk-1, VEGF receptor II;

Flt-1, fms-like tyrosine kinase-1, VEGF receptor I;

FLAG, epitope-tagging system for detection of target proteins or peptides;

HEC, human microvessel endothelial cells;

HRP, horseradish peroxidase;

IHC, immunohistochemistry;

MTT, 3-(4,5-dimethylthiazolyl-2)-2,5-diphenyltetrazolium bromide-based viability assay;

PBS, phosphate-buffered saline;

PlGF, placental growth factor;

RT, room temperature;

RTKs, receptor tyrosine kinases;

UT, untreated controls;

VEGF, vascular endothelial growth factor.

Placenta Growth Factor (PlGF) In Tumor Angiogenesis and Metastasis

Various embodiments of the present invention concern compositions and methods directed towards placenta growth factor (PlGF), a member of the VEGF family of growth factors. In certain embodiments, inhibitors (ligands) targeted to PlGF or targeted to PlGF and Flt-1 are of use to inhibit tumor angiogenesis and/or metastasis.

PlGF has a 53% identity with the platelet-derived growth factor-like region of VEGF (Maglione et al., 1991, *Proc Natl Acad Sci USA* 88:9267-9271). It is produced as two main isoforms, PlGF-1 and -2. These are secreted as dimers composed of 132 or 153 amino acid monomers linked in a head-to-tail fashion by disulfide bonds (Maglione et al., 1991), for a total weight of 46-50 kD. Three isoforms result from mRNA splice variants, but only PlGF-1 and -2 are well characterized (Ahmed et al., 2000; Cao et al., 1997, *Biochem Biophys Acta* 235, 493-498).

First cloned from placenta (Maglione et al., 1991), PlGF is normally expressed by trophoblasts, normal thyroid, and during wound healing (Viglietto et al., 1995, *Oncogene* 11:1569-1579; Fulla et al., 2000, *J Invest Dermatol* 115:388-395). In trophoblasts, PlGF expression is abrogated by hypoxic stress (Gleadle et al., Am. J. Physiol. 268:C1362-8, 1995) but hypoxia-driven expression has been found in at least one primary tumor (Yonekura et al., J. Biol. Chem. 274:35172-8, 1999), in tumor xenografts (Taylor et al., Clin. Cancer Res. 61:2696-703, 2001), and in fibroblasts (Green et al., Cancer Res. 61:2696-703, 2001). Many malignancies express the PlGF receptor, Flt-1 (Luttun et al., Nat. Med. 8:831-40, 2002).

PlGF is found in low levels in normal serum, but undergoes a 9-10-fold increase in the serum of women without pre-eclampsia in late pregnancy (Helske et al., 2001, *Mol Hum Reprod* 7:205-210; Reuvekamp et al., 1999, *Br J Obstet Gynaecol* 106:1019-1022; Vuorela-Vepsalainen et al., 1999, *Hum Reprod* 14:1346-1351). PlGF has been detected in glioblastomas and meningiomas, even though it is not expressed in normal brain tissue (Gleadle et al., 1995, *Am J Physiol* 268:C1362-1368; Donnini et al., 1999, *J Pathol* 189:66-71). It has also been detected in a variety of other primary malignancies (Nomura et al., 1998, *J. Neurooncol.* 40:123-30; Taylor et al., 2003a, *Proc Am Assoc Cancer Res* 44:4-5 [abstr R22]; Matsumoto et al., 2003, *Anticancer Res* 23:3767-3773; Chen et al., 2004, *Cancer Lett* 213:73-82; Wei et al., 2005, *Gut* 54, 666-672; Lacal et al., 2000, *J Invest Dermatol* 115, 1000-1007). PlGF expression has also been observed associated with diabetic retinopathy with neovascular proliferation (Khaliq et al., 1998, *Lab Invest.* 78:109-16). Deletion experiments with PlGF showed an inhibition of tumor growth and reduction of retinal neovascularization in animal models (Carmeliet et al., 2001, *Nat. Med.* 7:575-83).

PlGF-1, which lacks a heparin-binding domain, binds only to Flt-1 (also termed VEGFR1), while PlGF-2, which has a 21-amino-acid heparin-binding domain at the COOH terminus, binds both neuropilin-1 and Flt-1 (Migdala et al., 1998, *J Biol Chem* 273:22272-22278; Hauser and Weich, 1993, *Growth Factors* 9:259-268). When bound to Flt-1, PlGF-2 is capable of inducing differentiation, proliferation, and migration of endothelial cells (Landgren et al., 1998, *Oncogene* 16:359-367). In trophoblasts, expression of PlGF is abrogated by hypoxic stress (Gleadle et al., 1995), but hypoxia-driven expression has been found in at least one primary tumor (Yonekura et al., 1999, *J Biol Chem* 274:35172-35178), in tumor xenografts (Taylor et al., 2004, *Proc Am Assoc Cancer Res* 45:981 [abstr 4255]), and in fibroblasts (Green et al., 2001, *Cancer Res* 61:2696-2703). Both PlGF-1 and -2 naturally form heterodimers with VEGF. The relative activity of the heterodimers may depend on the form of PlGF that is bound to VEGF. Heterodimers consisting of the PlGF-1 isomer and VEGF have little or no activity in vitro or in vivo (Eriksson et al., 2002, *Cancer Cell* 1:99-108). On the other hand, PlGF-2/VEGF heterodimers are almost as potent as VEGF homodimers (Clauss et al., 1996, *J Biol Chem* 271:17629-17634; Cao et al., 1996, *J Biol Chem* 271:3154-3162; DiSalvo et al., 1995, *J Biol Chem* 270:7717-7723).

The receptor for PlGF (and for VEGF), Flt-1, is a member of the tyrosine kinase family of receptors (RTKs). These are characterized by autophosphorylation of tyrosine residues in their cytoplasmic domains when bound by an activating ligand. Flt-1 has seven extracellular Ig-like domains, and a split intracellular tyrosine kinase domain. The interaction of Flt-1 with PlGF lies mainly in the second extracellular domain. The fourth domain of Flt-1 is associated with dimerization, and contains a heparin-binding region that potentially brings Flt-1 and its ligand into closer association (Park and Lee, 1999, *Biochem Biophys Res Commun* 264:730-734). The anti-parallel PlGF dimer assures that the binding domains are at opposite ends of the dimer, and thus, when binding, Flt-1 most likely brings two receptors into close association, linking them for activation (Fuh et al., 1998, *J Biol Chem* 273:11197-11204; Wiesmann et al., 1997, Cell 91:695-704).

Heparin interactions with the heparin-binding domains of PlGF and Flt-1 may be essential for full activation of Flt-1 by PlGF. The role of heparin binding is well characterized in the fibroblast growth factor (FGF)-fibroblast growth factor receptor (FGFR) ligand-tyrosine kinase receptor pair (Schlessinger et al., 2000, *Molecular Cell* 6:743-750). In this example, heparin makes multiple contacts with both the ligand and the receptor, which increases FGF-FGFR binding to each other and dimerization of the receptors, a necessary step in activation. The presence of heparin-binding domains on the more active form of PlGF, PlGF-2, suggests that heparin may have a role in the activation of Flt-1 by PlGF.

In our investigation of tumor recurrence, we detected PlGF production by surviving tumor cells following cytotoxic treatment with radiolabeled antibodies (Taylor et al., 2002a; Taylor et al., 2003; Taylor et al., 2002b, *Proc Am Assoc Cancer Res* 43:10-11 [abstr 51]), even when PlGF expression was undetectable before treatment. It is already established that PlGF is a survival factor for endothelial cells (Adini et al., 2002, *Cancer Res* 62:2749-2752), but its treatment-induced expression by tumor cells was an unexpected finding (Taylor et al., 2002a; Taylor et al., 2003b, *Int J Cancer* 105:158-169). Further investigation correlated PlGF expression with enhanced recovery from cytotoxic treatment (Taylor et al., 2003b). Treatment-induced as well as constitutive expression by some tumor cell lines was also found.

Hypoxia, a condition ubiquitous in tumors due to metabolic activity or treatment, results in increased PlGF expression by keratinocytes and tumor cells (Ahmed et al., 2000; Taylor et al., 2002a; Taylor et al., 2003b). Some malignant cells express low levels of Flt-1 on their surface, yet the direct effects of signaling through the ligand-receptor are not well characterized. These findings suggested that PlGF might exert effects on tumor cells and in the tumor environment. The present disclosure examined the direct effects of PlGF and Flt-1 on human breast cancer cells and xenografts.

Relative Roles of PlGF and VEGF in Angiogenesis

Both PlGF and VEGF bind to the Flt-1 receptor and both have been reported to stimulate angiogenesis in tumor and normal tissues. The effect of VEGF binding to the Flt-1 receptor on angiogenesis has been examined (El-Mousawi et al., 2003, *J Biol. Chem.* 278:46681-91; U.S. Patent Application publication No. 20040266694). El-Mousawi et al. (2003) used a random 16-mer phage display system panned against recombinant Flt-1 to isolate several apparent VEGF-binding peptides. The strongest interaction was observed with a peptide designated V5.2. Addition of V5.2 to HUVEC and HCEC endothelial cells stimulated with VEGF or PlGF was reported to inhibit endothelial cell proliferation and was also reported to inhibit VEGF-mediated migration of HCECs and VEGF-induced capillary formation in Matrigel™ (El-Mousawi et al., 2003). It was suggested that these effects of V5.2 were mediated through binding to the Flt-1 receptor (Id.). However, the domain of Flt-1 that bound to V5.2 was not characterized by these authors, and it was not determined whether the V5.2 effects were antagonistic with heparin activation of Flt-1. In various embodiments, where administration of a PlGF ligand in combination with another anti-angiogenic agent, such as an anti-VEGF agent, is contemplated, peptide V5.2 and similar VEGF inhibitors may be of use.

The roles of VEGF-A, VEGF-B and PlGF in angiogenesis were examined by Malik et al., "Redundant roles of VEGF-B and PlGF during selective VEGF-A blockade in mice," Blood, published online Sep. 27, 2005. These authors reported that mice lacking either VEGF-B or PlGF display only minor developmental defects. Inhibition of VEGF-A activity, compared to inhibition of VEGF-A, VEGF-B and PlGF, resulted in similar effects on growth and survival of neonatal mice, including a reduction in vascularization. It was concluded that PlGF and VEGF-B do not compensate for blockade of VEGF-A, indicating that VEGF-B and PlGF activation of the VEGFR-1 receptor plays a relatively minor role in postnatal development and adult vascular homeostasis compared to VEGF-A activation of VEGFR-2. These results conflicted with other reports that antibodies against VEGFR-1 were almost as effective as anti-VEGFR-2 antibodies in inhibiting xenograft tumor growth and angiogenesis (Carmeliet et al., 2001, *Nat. Med.* 7:575-83; Stefanik et al., 2001, *J. Neurooncol.* 55:91-100). It was suggested that VEGF-B and PlGF may be involved in regulation of inflammatory events during pathologic angiogenesis in adults (Malik et al., 2005).

The skilled artisan will realize that the PlGF ligands disclosed herein may be used in combination with one or more VEGF inhibitors. VEGF inhibitors of potential use include Neovastat® (Falardeau et al., 2001, *Semin. Oncol.* 28:620-25), IM862 (Tupule et al., 2000, *J. Clin. Oncol.* 18:716-23), Angiozyme™ (RPI-4610) (Weng and Usman, 2001, *Curr. Oncol. Rep.* 3:141-46), Bevacizumab (Gordon et al., 2001, *J. Clin Oncol.* 19:843-50), Semaxanib (SU-5416) (Fong et al., 1999, *Cancer Res.* 59:99) and TNP-470 (Figg et al., 1997, *Pharmocotherapy* 17:91-97.

Therapeutic Treatment of Subjects by Inhibiting Angiogenesis

In various embodiments, the methods and compositions relating to PlGF ligands that can block or inhibit PlGF-mediated angiogenesis find application in treatment of those conditions characterized by pathological angiogenesis. Examples of these conditions include, but are not limited to, rheumatoid arthritis, inflammatory bowel disease, Crohn's disease, ulcerative colitis, sarcoidosis, asthma, edema, pulmonary hypertension, formation and development of tumors, psoriasis, diabetic retinopathy, macular degeneration, corneal graft rejection, neovascular glaucoma, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis, wound granulation, and tumor angiogenesis, growth and survival. Not all subjects with an angiogenesis- or cell motility-related disease state will express PlGF in diseased tissues, and the skilled artisan will realize that in certain embodiments, ex vivo and/or in vivo PlGF expression assays may be utilized to identify those subjects who would benefit most from PlGF-targeted therapeutic intervention.

The skilled artisan will realize that anti-angiogenic therapies may utilize one or more of the PlGF ligands disclosed herein, and in certain alternative embodiments may comprise the administration of other anti-angiogenic agents known in the art, such as Endostatin™, angiostatin, laminin peptides, fibronectin peptides (including ED-B fibronectin), plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, paclitaxel, accutin, angiostatin, cidofovir, vincristine, bleomycin, AGM-1470, platelet factor 4 or minocycline.

The skilled artisan will also realize that within the context of treating subjects with tumors, the PlGF ligands disclosed herein may be used in combination with any known cancer therapy, as discussed in more detail below. Known cancer therapies include, but are not limited to, administration of chemotherapeutic agents, radiation therapy, surgical excision, localized hyperthermia, anti-tumor antibodies and other anti-angiogenic agents.

Peptide Administration

Various embodiments of the claimed methods and/or compositions may concern one or more therapeutic peptides to be administered to a subject. Administration may occur by any route known in the art, including but not limited to oral, nasal, buccal, inhalational, rectal, vaginal, topical, orthotopic, intradermal, subcutaneous, intramuscular, intraperitoneal, intraarterial, intrathecal or intravenous injection.

Unmodified peptides administered orally to a subject can be degraded in the digestive tract and depending on sequence and structure may exhibit poor absorption across the intestinal lining. However, methods for chemically modifying peptides to render them less susceptible to degradation by endogenous proteases or more absorbable through the alimentary tract are well known (see, for example, Blondelle et al., 1995, Biophys. J. 69:604-11; Ecker and Crooke, 1995, Biotechnology 13:351-69; Goodman and Ro, 1995, BURGER'S MEDICINAL CHEMISTRY AND DRUG DISCOVERY, VOL. I, ed. Wollf, John Wiley & Sons; Goodman and Shao, 1996, Pure & Appl. Chem. 68:1303-08). Such methods can be performed on peptides that bind to a selected target, such as PlGF. Methods for preparing libraries of peptide analogs, such as peptides containing D-amino acids; peptidomimetics consisting of organic molecules that mimic the structure of a peptide; or peptoids such as vinylogous peptoids, have also been described and may be used to construct PlGF binding peptides suitable for oral administration to a subject.

In certain embodiments, preparation and administration of peptide mimetics that mimic the structure of known PlGF ligands, such as BP-1, BP-2, BP-3 or BP-4, may be used within the scope of the claimed methods and compositions. In such compounds, the standard peptide bond linkage may be replaced by one or more alternative linking groups, such as $CH_2$—NH, $CH_2$—S, $CH_2$—$CH_2$, CH═CH, CO—$CH_2$, CHOH—$CH_2$ and the like. Methods for preparing peptide mimetics are well known (for example, Hruby, 1982, *Life Sci* 31:189-99; Holladay et al., 1983, *Tetrahedron Lett.* 24:4401-

04; Jennings-White et al., 1982, *Tetrahedron Lett.* 23:2533; Almquiest et al., 1980, *J. Med. Chem.* 23:1392-98; Hudson et al., 1979, *Int. J. Pept. Res.* 14:177-185; Spatola et al., 1986, *Life Sci* 38:1243-49; U.S. Pat. Nos. 5,169,862; 5,539,085; 5,576,423, 5,051,448, 5,559,103, each incorporated herein by reference.) Peptide mimetics may exhibit enhanced stability and/or absorption in vivo compared to their peptide analogs.

Alternatively, therapeutic peptides may be administered by oral delivery using N-terminal and/or C-terminal capping to prevent exopeptidase activity. For example, the C-terminus may be capped using amide peptides and the N-terminus may be capped by acetylation of the peptide. Peptides may also be cyclized to block exopeptidases, for example by formation of cyclic amides, disulfides, ethers, sulfides and the like.

Peptide stabilization may also occur by substitution of D-amino acids for naturally occurring L-amino acids, particularly at locations where endopeptidases are known to act. Endopeptidase binding and cleavage sequences are known in the art and methods for making and using peptides incorporating D-amino acids have been described (e.g., U.S. Patent Application Publication No. 20050025709, McBride et al., filed 2/305, incorporated herein by reference). Another alternative would use a cyclic peptide comprising the sequence of BP-1, BP-2, BP-3 or BP-4 flanked by cysteine residues and comprised of all D-amino acids. Such a D-amino acid cyclic analog may have the same folded conformation as the L-form, which may be assessed by computer modeling studies using techniques known in the art. In preferred embodiments, the modified peptides will exhibit PlGF binding in the nanomolar or lower range. Modified peptides may be assayed for PlGF binding by standard assays, such as ELISA. The skilled artisan will be aware that peptide modification should be followed by testing for target binding activity to direct the course of peptide modification. In certain embodiments, peptides and/or proteins may be orally administered by co-formulation with proteinase- and/or peptidase-inhibitors.

Other methods for oral delivery of therapeutic peptides are disclosed in Mehta ("Oral delivery and recombinant production of peptide hormones," June 2004, *BioPharm International*). The peptides are administered in an enteric-coated solid dosage form with excipients that modulate intestinal proteolytic activity and enhance peptide transport across the intestinal wall. Relative bioavailability of intact peptides using this technique ranged from 1% to 10% of the administered dosage. Insulin, a much larger protein than the PlGF binding peptides disclosed herein, has been successfully administered in dogs using enteric-coated microcapsules with sodium cholate and a protease inhibitor (Ziv et al., 1994, *J. Bone Miner. Res.* 18 (Suppl. 2):792-94. Oral administration of peptides has been performed using acylcarnitine as a permeation enhancer and an enteric coating (Eudragit L30D-55, Rohm Pharma Polymers, see Mehta, 2004). Excipients of use for orally administered peptides may generally include one or more inhibitors of intestinal proteases/peptidases along with detergents or other agents to improve solubility or absorption of the peptide, which may be packaged within an enteric-coated capsule or tablet (Mehta, 2004). The enteric coating is resistant to acid, allowing the peptide to pass through the stomach into the intestine for absorption. Organic acids may be included in the capsule to acidify the intestine and inhibit intestinal protease activity once the capsule dissolves in the intestine (Mehta, 2004). Another alternative for oral delivery of peptides would include conjugation to polyethylene glycol (PEG)-based amphiphilic oligomers, increasing absorption and resistance to enzymatic degradation (Soltero and Ekwuribe, 2001, *Pharm. Technol.* 6:110).

In still other embodiments, peptides such as PlGF binding peptides may be modified for oral or inhalational administration by conjugation to certain proteins, such as the Fc region of IgG1 (see Examples 3-7). Methods for preparation and use of peptide-Fc conjugates are disclosed, for example, in Low et al. (2005, *Hum. Reprod.* 20:1805-13) and Dumont et al. (2005, *J. Aerosol. Med.* 18:294-303), each incorporated herein by reference. Low et al. (2005) disclose the conjugation of the alpha and beta subunits of FSH to the Fc region of IgG1 in single chain or heterodimer form, using recombinant expression in CHO cells. The Fc conjugated peptides were absorbed through epithelial cells in the lung or intestine by the neonatal Fc receptor mediated transport system. The Fc conjugated peptides exhibited improved stability and absorption in vivo compared to the native peptides. It was also observed that the heterodimer conjugate was more active than the single chain form. Larger proteins, such as erythropoietin, may also be effectively delivered by inhalation using Fc conjugation (Dumont et al., 2005).

In alternative embodiments, therapeutic peptides may be administered by an inhalational route (e.g., Sievers et al., 2001, *Pure Appl. Chem.* 73:1299-1303). Supercritical carbon dioxide aerosolization has been used to generate nano or micro-scale particles out of a variety of pharmaceutical agents, including proteins and peptides (Id.) Microbubbles formed by mixing supercritical carbon dioxide with aqueous protein or peptide solutions may be dried at lower temperatures (25 to 65° C.) than alternative methods of pharmaceutical powder formation, retaining the structure and activity of the therapeutic peptide (Id.) In some cases, stabilizing compounds such as trehalose, sucrose, other sugars, buffers or surfactants may be added to the solution to further preserve functional activity. The particles generated are sufficiently small to be administered by inhalation, avoiding some of the issues with intestinal proteases/peptidases and absorption across the gastrointestinal lining.

Dosages of therapeutic peptides to be administered to a subject may vary, depending upon the pharmacodynamic characteristics, the mode and route of administration, age, weight and health of the subject, the nature and extent of symptoms, concurrent therapy and frequency of treatment. Dosages of peptides may range between about 1 and 3000 mg per 50 kg body weight, preferably 10 to 1000 mg/50 kg, more preferably 25 to 800 mg/50 kg. A dose of between 8 and 800 mg/50 kg may be administered divided into 1 to 6 doses per day or in a sustained release form. In one study, a single 500 gg dose of peptide administered to human subjects resulted in peak plasma concentrations ranging from about 150 to 600 pg/ml within 90 to 180 minutes (Mehta, 2004).

Phage Display

Certain embodiments of the claimed compositions and/or methods concern binding peptides and/or peptide mimetics of various protein targets, such as PlGF. PlGF binding peptides (BP) may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807, incorporated herein by reference.

Proteins and Peptides

A variety of polypeptides or proteins may be used within the scope of the claimed methods and compositions. In certain embodiments, the proteins may comprise antibodies or fragments of antibodies containing an antigen-binding site. In other embodiments, a short peptide ligand of a target, such as PlGF, may be used for a variety of purposes, such as detecting the presence of PlGF receptors on a cell, tissue or organ, inhibiting or blocking binding of PlGF to its receptor(s), facilitating or activating binding of PlGF to its receptors, or mimicking part of the PlGF molecule or its receptor(s).

As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the 20 common amino acids found in naturally occurring proteins, or at least one modified or unusual amino acid.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 4 below.

TABLE 4

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Alle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes, such as the PlGF gene, have been previously disclosed and may be found at computerized databases known to those of ordinary skill in the art. One such database is the National Center for Biotechnology Information's Genbank and GenPept databases (www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides, and peptides are known to those of skill in the art.

Peptide Mimetics

Another embodiment for the preparation of polypeptides is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993), incorporated herein by reference. The rationale behind the use of peptide mimetics is that the peptide backbone of proteins exists chiefly to orient amino acid side chains so as to facilitate molecular interactions, such as those of antibody and antigen. A peptide mimetic is expected to permit molecular interactions similar to the natural molecule. These principles may be used to engineer second generation molecules having many of the natural properties of the binding peptides disclosed herein, but with altered or improved characteristics, such as increased absorption across the stomach or intestine and/or improved stability or activity in vivo.

Fusion Proteins

Various embodiments may concern fusion proteins. These molecules generally have all or a substantial portion of a peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope. Yet another useful form of fusion may include attachment of a moiety of use for purification, such as the FLAG epitope (Prickett et al., 1989, *Biotechniques* 7:580-589; Castrucci et al., 1992, *J Virol* 66:4647-4653). Methods of generating fusion proteins are well known to those of skill in the art. Such proteins may be produced, for example, by chemical attachment using bifunctional cross-linking reagents, by de novo synthesis of the complete fusion protein, or by attachment of a DNA sequence encoding a first protein or peptide to a DNA sequence encoding a second peptide or protein, followed by expression of the intact fusion protein.

Protein Purification

In some embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast protein liquid chromatography (FPLC) or even HPLC.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix, such as a magnetic bead (Dynal) or a Sepharose or Sephadex bead (Pharmacia). The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthetic Peptides

Proteins or peptides may be synthesized, in whole or in part, in solution or on a solid support in accordance with conventional techniques. Various automatic synthesizers are commercially available and can be used in accordance with known protocols. See, for example, Stewart and Young, (1984, *Solid Phase Peptide Synthesis*, 2d. ed., Pierce Chemical Co.); Tam et al., (1983, *J. Am. Chem. Soc.*, 105:6442); Merrifield, (1986, *Science*, 232: 341-347); and Barany and Merrifield (1979, *The Peptides*, Gross and Meienhofer, eds., Academic Press, New York, pp. 1-284). Short peptide sequences, usually from about 6 up to about 35 to 50 amino acids, can be readily synthesized by such methods. Alternatively, recombinant DNA technology may be employed wherein a nucleotide sequence which encodes a peptide of interest is inserted into an expression vector, transformed or transfected into an appropriate host cell, and cultivated under conditions suitable for expression.

Antibodies

Various embodiments may concern antibody ligands for a target, such as anti-PlGF antibodies. The term "antibody" is used herein to refer to any antibody-like molecule that has an antigen binding region, and includes antibody fragments such as Fab', Fab, $F(ab')_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.).

Polyclonal Antibodies

Polyclonal antibodies may be prepared by immunizing an animal with an immunogen and collecting antisera from that immunized animal. A wide range of animal species may be used for the production of antisera. Typically an animal used for production of antisera is a non-human animal, for example, rabbits, mice, rats, hamsters, pigs or horses. Because of the relatively large blood volume of rabbits, a rabbit is a preferred choice for production of polyclonal antibodies.

Antibodies, both polyclonal and monoclonal, may be prepared using conventional immunization techniques. A composition containing antigenic epitopes may be used to immunize one or more experimental animals, such as a rabbit or mouse, which will then proceed to produce specific antibodies. Polyclonal antisera may be obtained, after allowing time for antibody generation, simply by bleeding the animal and preparing serum samples from the whole blood.

A given composition may vary in its immunogenicity. It is often necessary, therefore, to boost the host immune system, as may be achieved by coupling an immunogen to a carrier. Exemplary and preferred carriers are keyhole limpet hemocyanin (KLH) and bovine serum albumin (BSA). Other albumins such as ovalbumin, mouse serum albumin or rabbit serum albumin also may be used as carriers. Means for conjugating an antigen to a carrier protein are well known and include cross-linkers such as glutaraldehyde, m-maleimidobenzoyl-N-hydroxysuccinimide ester, carbodiimide and bis-biazotized benzidine.

The immunogenicity of a particular immunogen composition may be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes may be used to administer the immunogen (subcutaneous, intramuscular, intradermal, intravenous and intraperitoneal). The production of polyclonal antibodies may be monitored by sampling blood of the immunized animal at various points following immunization. A second, booster, injection also may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Monoclonal Antibodies

Monoclonal antibodies may be readily prepared through use of well-known techniques, such as those exemplified in U.S. Pat. No. 4,196,265. Typically, this technique involves immunizing a suitable animal with a selected immunogen composition. The immunizing composition is administered in a manner effective to stimulate antibody producing cells. Cells from rodents such as mice and rats are preferred. Mice are more preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B-lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art. For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus, and those using polyethylene glycol (PEG), such as 37% (v/v) PEG, have been described. The use of electrically induced fusion methods is also appropriate.

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines also could be cultured in vitro, where the mAbs are naturally secreted into the culture medium from which they can be readily obtained in high concentrations. mAbs produced by either means may be further purified, if desired, using filtration, centrifugation, and various chromatographic methods such as HPLC or affinity chromatography.

Production of Antibody Fragments

Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Chimeric and Humanized Antibodies

A chimeric antibody is a recombinant protein in which the variable regions of a human antibody have been replaced by the variable regions of, for example, an anti-PlGF mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

In another embodiment, an antibody may be a human monoclonal antibody. Such antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique, as discussed above, may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual,* Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as discussed above. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled, for example, to PlGF ligands by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Bi-Specific Antibodies and Conjugates

In certain embodiments, the PlGF ligands disclosed herein may be used in combination with another molecule attached to the ligand. Attachment may be either covalent or non-covalent. In some embodiments, a PlGF ligand may be attached to a bi-specific antibody, i.e., an antibody that has two different binding sites, one for the PlGF ligand and another for a disease-related target antigen. Any disease or condition relating to angiogenesis, cancer, metastasis or cell motility may be targeted, including but not limited to, primary cancer, metastatic cancer, hyperplasia, rheumatoid arthritis, inflammatory bowel disease, Crohn's disease, ulcerative colitis, sarcoidosis, asthma, edema, pulmonary hypertension, formation and development of tumor tissue, psoriasis, diabetic retinopathy, macular degeneration, corneal graft rejection, neovascular glaucoma, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis and wound granulation. Methods for construction and use of bi-specific and multi-specific antibodies are disclosed, for example, in U.S. Patent Application Publication No. 20050002945, filed Feb. 11, 2004, the entire text of which is incorporated herein by reference.

Where the bi-specific antibody is targeted in part against a tumor-associated antigen, it is anticipated that any type of tumor and any type of tumor antigen may be so targeted. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer. Preferred are tumors that have constitutive expression of PlGF, or which can be stimulated to produce PlGF.

Tumor-associated antigens that may be targeted include, but are not limited to, A3, antigen specific for A33 antibody, BrE3-antigen, CD1, CD1a, CD3, CD5, CD15, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, 5100, TAG-72, p53, tenascin, IL-6, IL-8, insulin growth factor-1 (IGF-1), Tn antigen, Thomson-Friedenreich antigens, tumor necrosis antigens, VEGF, 17-1A-antigen, an angiogenesis marker (e.g., ED-B fibronectin), an oncogene marker, an oncogene product, and other tumor-associated antigens. Recent reports on tumor associated antigens include Mizukami et al., (2005, *Nature Med.* 11:992-97); Hatfield et al., (2005, *Curr. Cancer Drug Targets* 5:229-48); Vallbohmer et al. (2005, *J. Clin. Oncol.* 23:3536-44) and Ren et al. (2005, *Ann. Surg.* 242:55-63), each incorporated herein by reference.

A variety of recombinant methods can be used to produce bi-specific antibodies and antibody fragments. For example, bi-specific antibodies and antibody fragments can be produced in the milk of transgenic livestock. (See, e.g., Colman, A., Biochem. Soc. Symp., 63: 141-147, 1998; U.S. Pat. No. 5,827,690, each incorporated herein by reference.) Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow alpha-lactoglobulin gene, the sheep beta-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Pre-Targeting

One strategy for use of bi-specific antibodies includes pre-targeting methodologies, in which an effector molecule, such as an anti-angiogenic or anti-tumor PlGF ligand, is administered to a subject after a bi-specific antibody has been administered. The bi-specific antibody, which would include a binding site for the PlGF ligand and one for the diseased tissue, localizes to the diseased tissue and increases the specificity of localization of the effector PlGF ligand to the diseased tissue (U.S. Patent Application No. 20050002945). Because the effector molecule may be cleared from circulation much more rapidly than the bi-specific antibody, normal tissues may have a decreased exposure to the effector molecule when a pretargeting strategy is used than when the effector molecule is directly linked to the disease targeting antibody.

Pretargeting methods have been developed to increase the target:background ratios of detection or therapeutic agents. Examples of pre-targeting and biotin/avidin approaches are described, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. No. 6,077,499; U.S. Ser. No. 09/597,580; U.S. Ser. No. 10/361,026; U.S. Ser. No. 09/337,756; U.S. Ser. No. 09/823,746; U.S. Ser. No. 10/116,116; U.S. Ser. No. 09/382,186; U.S. Ser. No. 10/150,654; U.S. Pat. No. 6,090,381; U.S. Pat. No. 6,472,511; U.S. Ser. No. 10/114,315; U.S. Provisional Application No. 60/386,411; U.S. Provisional Application No. 60/345,641; U.S. Provisional Application No. 60/3328,835; U.S. Provisional Application No. 60/426,379; U.S. Ser. No. 09/823,746; U.S. Ser. No. 09/337,756; and U.S. Provisional Application No. 60/342,103, all of which are incorporated herein by reference.

In certain embodiments, bispecific antibodies and targetable constructs may be of use in treating and/or imaging normal or diseased tissue and organs, for example using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, each incorporated herein by reference. Additional methods are described in U.S. application Ser. No. 09/337,756 filed Jun. 22, 1999 and in U.S. application Ser. No. 09/823,746, filed Apr. 3, 2001.

Targeting Peptides

In other embodiments, peptide PlGF ligands such as BP-1, BP-2, BP-3 or BP-4 may be used as targeting peptides for delivery of one or more agents to a diseased tissue. In such case, the agent may be covalently or non-covalently attached to the PlGF binding peptide. Agents of potential use include drugs, prodrugs, toxins, enzymes, oligonucleotides, radioisotopes, immunomodulators, cytokines, hormones, binding molecules, lipids, polymers, micelles, liposomes, nanoparticles, or combinations thereof. Exemplary therapeutic agents and methods of use are disclosed in U.S. Patent Publication Nos. 20050002945, 20040018557, 20030148409 and 20050014207, each incorporated herein by reference.

In exemplary embodiments, agents of use may comprise one or more of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, Pseudomonas exotoxin, Pseudomonas endotoxin, an antisense oligonucleotide, an interference RNA, or a combination thereof.

Aptamers

In certain embodiments, a PlGF ligand of use may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the PlGF-binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)$NR_2$, P(O)R, P(O)OR', CO, or $CNR_2$, wherein R is H or alkyl (1-20C) and R' is alkyl (1-20C); in addition, this group may be attached to adjacent nucleotides through O or S, Not all linkages in an oligomer need to be identical.

The aptamers used as starting materials in the process of the invention to determine specific binding sequences may be single-stranded or double-stranded DNA or RNA. In a preferred embodiment, the sequences are single-stranded DNA, which is less susceptible to nuclease degradation than RNA. In preferred embodiments, the starting aptamer will contain a randomized sequence portion, generally including from about 10 to 400 nucleotides, more preferably 20 to 100 nucleotides. The randomized sequence is flanked by primer sequences that permit the amplification of aptamers found to bind to the target. For synthesis of the randomized regions, mixtures of nucleotides at the positions where randomization is desired may be added during synthesis.

Methods for preparation and screening of aptamers that bind to particular targets of interest are well known, for example U.S. Pat. No. 5,475,096 and U.S. Pat. No. 5,270,163, each incorporated by reference. The technique generally involves selection from a mixture of candidate aptamers and step-wise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) are retained during separation. Each cycle results in an enrichment of aptamers with high affinity for the target. Repetition for between three to six selection and amplification cycles may be used to generate aptamers that bind with high affinity and specificity to the target, such as PlGF.

Methods of Disease Tissue Detection, Diagnosis and Imaging

Protein Based In Vitro Diagnosis

The present invention contemplates the use of PlGF ligands, including PlGF binding peptides, PlGF fusion proteins, PlGF antibodies or fragments, bi-specific antibodies and antibody fragments, to screen biological samples in vitro and/or in vivo for the presence of the PlGF antigen. In exemplary immunoassays, the PlGF antibody, fusion protein, or fragment thereof may be utilized in liquid phase or bound to a solid-phase carrier, as described below. In preferred embodiments, particularly those involving in vivo administration, the PlGF antibody or fragment thereof is humanized. Also preferred, the PlGF antibody or fragment thereof is fully human. Still preferred, the PlGF fusion protein comprises a humanized or fully human PlGF antibody. The skilled artisan will realize that a wide variety of techniques are known for determining levels of expression of a particular gene and any such known method, such as immunoassay, RT-PCR, mRNA purification and/or cDNA preparation followed by hybridization to a gene expression assay chip may be utilized to determine levels of PlGF expression in individual subjects and/or tissues.

One example of a screening method for determining whether a biological sample contains the PlGF antigen is radioimmunoassay (RIA). For example, in one form of RIA, the substance under test is mixed with PlGF MAb in the presence of radiolabeled PlGF antigen. In this method, the concentration of the test substance will be inversely proportional to the amount of labeled PlGF antigen bound to the MAb and directly related to the amount of free, labeled PlGF antigen. Other suitable screening methods will be readily apparent to those of skill in the art.

Alternatively, in vitro assays may be performed in which a PlGF ligand, anti-PlGF antibody, fusion protein, or fragment thereof is bound to a solid-phase carrier. For example, MAbs can be attached to a polymer, such as aminodextran, in order to link the MAb to an insoluble support such as a polymer-coated bead, a plate or a tube.

The presence of the PlGF antigen in a biological sample may be determined using an enzyme-linked immunosorbent assay (ELISA). In the direct competitive ELISA, a pure or semipure antigen preparation is bound to a solid support that is insoluble in the fluid or cellular extract being tested and a quantity of detectably labeled soluble antibody, antibody fragment or PlGF ligand is added to permit detection and/or quantitation of the binary complex formed between solid-phase antigen and labeled PlGF binding molecule.

A sandwich ELISA requires small amounts of antigen, and the assay does not require extensive purification of the antigen. Thus, the sandwich ELISA is preferred to the direct competitive ELISA for the detection of an antigen in a clinical sample. See, for example, Field et al., *Oncogene* 4:1463 (1989); Spandidos et al., *AntiCancer Res.* 9: 821 (1989).

In a sandwich ELISA, a quantity of unlabeled MAb or antibody fragment (the “capture antibody”) is bound to a solid support, the test sample is brought into contact with the capture antibody, and a quantity of detectably labeled soluble antibody (or antibody fragment) is added to permit detection and/or quantitation of the ternary complex formed between the capture antibody, antigen, and labeled antibody. An antibody fragment is a portion of an antibody such as $F(ab')_2$, $F(ab)_2$, Fab', Fab, and the like. In the present context, an antibody fragment is a portion of a PlGF MAb that binds to an epitope of the PlGF antigen. The term “antibody fragment” also includes any synthetic or genetically engineered protein that acts like an antibody by binding to a specific antigen to form a complex. For example, antibody fragments include isolated fragments consisting of the light chain variable region, “Fv” fragments consisting of the variable regions of the heavy and light chains, and recombinant single chain polypeptide molecules in which light and heavy variable regions are connected by a peptide linker. An antibody fusion protein is a recombinantly produced antigen-binding molecule in which two or more of the same or different single-chain antibody or antibody fragment segments with the same or different specificities are linked. The fusion protein may comprise a single antibody component, a multivalent or multispecific combination of different antibody components or multiple copies of the same antibody component. The fusion protein may additionally comprise an antibody or an antibody fragment conjugated to a diagnostic/detection and/or a therapeutic agent. The term PlGF antibody includes humanized, human and murine antibodies, antibody fragments thereof, immunoconjugates and fragments thereof and antibody fusion proteins and fragments thereof.

Methods of performing a sandwich ELISA are well-known. See, for example, Field et al., supra, Spandidos et al., supra, and Moore et al., “Twin-Site ELISAs for fos and myc Oncoproteins Using the AMPAK System,” in METHODS IN MOLECULAR BIOLOGY, VOL. 10, pages 273-281 (The Humana Press, Inc. 1992). The skilled artisan will realize that an assay similar to a sandwich ELISA may be performed by substituting PlGF ligand for either the first unlabeled antibody or the second labeled antibody.

In a sandwich ELISA, the soluble antibody or antibody fragment must bind to a PlGF epitope that is distinct from the epitope recognized by the capture antibody. The sandwich ELISA can be performed to ascertain whether the PlGF antigen is present in a biopsy sample. Alternatively, the assay can be performed to quantitate the amount of PlGF antigen that is present in a clinical sample of body fluid. The quantitative assay can be performed by including dilutions of purified PlGF antigen.

In other embodiments, Western blot analysis may be used to detect and quantify the presence of PlGF in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies or ligands that specifically bind PlGF. The anti-P1GF antibodies or ligands specifically bind to PlGF on the solid support. These antibodies or ligands may be directly labeled or alternatively may be subsequently detected using labeled secondary antibodies that specifically bind to the anti-PlGF antibody or ligand.

The PlGF ligands, Mabs, fusion proteins, and fragments thereof also are suited for the preparation of an assay kit. Such a kit may comprise a carrier means that is compartmentalized to receive in close confinement one or more container means such as vials, tubes and the like, each of said container means comprising the separate elements of the immunoassay. For example, there may be a container means containing the capture antibody immobilized on a solid phase support, and a further container means containing detectably labeled antibodies in solution. Further container means may contain standard solutions comprising serial dilutions of PlGF antigen. The standard solutions of PlGF antigen may be used to prepare a standard curve with the concentration of PlGF antigen plotted on the abscissa and the detection signal on the ordinate. The results obtained from a sample containing PlGF antigen may be interpolated from such a plot to give the concentration of PlGF antigen in the biological sample.

PlGF ligands, anti-PlGF antibodies, fusion proteins, and fragments thereof may also be used to detect the presence of the PlGF antigen in tissue sections prepared from a histological specimen. Such in situ detection can be used to determine the presence of the PlGF antigen and to determine the distribution of the PlGF antigen in the examined tissue. In situ detection can be accomplished by applying a detectably-labeled PlGF ligand or antibody to frozen or paraffin-embedded tissue sections. General techniques of in situ detection are well-known to those of ordinary skill. See, for example, Ponder, "Cell Marking Techniques and Their Application," in MAMMALIAN DEVELOPMENT: A PRACTICAL APPROACH 113-38 Monk (ed.) (IRL Press 1987), and Coligan at pages 5.8.1-5.8.8.

PlGF ligands, anti-PlGF antibodies, fusion proteins, and fragments thereof can be detectably labeled with any appropriate marker moiety, for example, a radioisotope, an enzyme, a fluorescent label, a dye, a chromagen, a chemiluminescent label, a bioluminescent label or a paramagnetic label. Methods of making and detecting such detectably-labeled PlGF antibodies are well-known to those of ordinary skill in the art, and are described in more detail below.

The marker moiety may be a radioisotope that is detected by such means as the use of a gamma counter or a beta-scintillation counter or by autoradiography. In a preferred embodiment, the diagnostic conjugate is a gamma-, beta- or a positron-emitting isotope. A marker moiety refers to a molecule that will generate a signal under predetermined conditions. Examples of marker moieties include radioisotopes, enzymes, fluorescent labels, chemiluminescent labels, bioluminescent labels and paramagnetic labels. The binding of marker moieties to PlGF antibodies can be accomplished using standard techniques known to the art. Typical methodology in this regard is described by Kennedy et al., Clin. Chim. Acta 70:1 (1976), Schurs et al., Clin. Chim. Acta 81: 1 (1977), Shih et al., Int'l J. Cancer 46: 1101 (1990).

Nucleic Acid Based In Vitro Diagnosis

In particular embodiments, nucleic acids may be analyzed to determine levels of PlGF expression, particularly using nucleic acid amplification methods. Nucleic acid sequences (mRNA and/or cDNA) to be used as a template for amplification may be isolated from cells contained in a biological sample, according to standard methodologies. The nucleic acid may be fractionated or whole cell RNA. Where RNA is used, it may be desired to convert the RNA to a complementary cDNA. In one embodiment, the RNA is whole cell RNA and is used directly as the template for amplification.

In one example, the determination of PlGF expression is performed by amplifying (e.g. by PCR) the PlGF mRNA or cDNA sequences and detecting and/or quantifying an amplification product by any methods known in the art, including but not limited to TaqMan assay (Applied Biosystems, Foster City, Calif.), agarose or polyacrylamide gel electrophoresis and ethidium bromide staining, hybridization to a microarray comprising a PlGF specific probe, Northern blotting, dot-blotting, slot-blotting, etc.

Various forms of amplification are well known in the art and any such known method may be used. Generally, amplification involves the use of one or more primers that hybridize selectively or specifically to a target nucleic acid sequence to be amplified.

Primers: The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred. Methods of primer design are well-known in the art, based on the design of complementary sequences obtained from standard Watson-Crick base-pairing (i.e., binding of adenine to thymine or uracil and binding of guanine to cytosine). Computerized programs for selection and design of amplification primers are available from commercial and/or public sources well known to the skilled artisan. Particular primer sequences of use in detecting PlGF expression are known (e.g., Regnault et al., 2003, *J. Physiol.* 550: 641-56). The skilled artisan will realize that the specific sequences disclosed therein are exemplary only and that alternative primer and/or probe sequences may be used in the practice of the claimed methods.

Amplification: A number of template dependent processes are available to amplify the marker sequences present in a given sample. One of the best-known amplification methods is the polymerase chain reaction (referred to as PCR) which is described in detail in U.S. Pat. Nos. 4,683,195, 4,683,202 and 4,800,159.

One embodiment of the invention may comprise obtaining a suitable sample from an individual and detecting a PlGF messenger RNA. Once the tissue sample is obtained the sample may be prepared for isolation of the nucleic acids by standard techniques (eg, cell isolation, digestion of outer membranes, Oligo dT isolation of mRNA etc.) The isolation of the mRNA may also be performed using kits known to the art (Pierce, AP Biotech, etc). A reverse transcriptase PCR amplification procedure may be performed in order to quantify an amount of mRNA amplified. Methods of reverse transcribing RNA into cDNA are well known and described in Sambrook et al., 1989. Alternative methods for reverse transcription utilize thermostable DNA polymerases.

The above-described in vitro and in situ detection methods may be used to assist in the diagnosis or staging of a pathological condition. For example, such methods can be used to detect tumors that express the PlGF antigen, such as metastatic cancer.

In Vivo Diagnosis

PlGF ligands and/or antibodies are of use for in vivo diagnosis. Methods of diagnostic imaging with labeled peptides or MAbs are well-known. For example, in the technique of immunoscintigraphy, PlGF ligands or antibodies are labeled with a gamma-emitting radioisotope and introduced into a patient. A gamma camera is used to detect the location and distribution of gamma-emitting radioisotopes. See, for example, Srivastava (ed.), RADIOLABELED MONOCLONAL ANTIBODIES FOR IMAGING AND THERAPY (Plenum Press 1988), Chase, "Medical Applications of Radioisotopes," in REMINGTON'S PHARMACEUTICAL SCIENCES, 18th Edition, Gennaro et al. (eds.), pp. 624-652 (Mack Publishing Co., 1990), and Brown, "Clinical Use of Monoclonal Antibodies," in BIOTECHNOLOGY AND PHARMACY 227-49, Pezzuto et al. (eds.) (Chapman & Hall 1993). Also preferred is the use of positron-emitting radionuclides (PET isotopes), such as with an energy of 511 keV, such as fluorine-18 $^{18}$F), gallium-68 ($^{68}$Ga), and iodine-124 ($^{124}$I) Such imaging can be conducted by direct labeling of the PlGF ligand, or by a pretargeted imaging method, as described in Goldenberg et al, "Antibody Pretargeting Advances Cancer Radioimmunodetection and Radiotherapy," (submitted MS), see also U.S. Patent Publication Nos. 20050002945, 20040018557, 20030148409 and 20050014207, each incorporated herein by reference.

For diagnostic imaging, radioisotopes may be bound to the PlGF ligand or antibody either directly, or indirectly by using an intermediary functional group. Useful intermediary functional groups include chelators such as ethylenediaminetetraacetic acid and diethylenetriaminepentaacetic acid. For example, see Shih et al., supra, and U.S. Pat. No. 5,057,313.

The radiation dose delivered to the patient is maintained at as low a level as possible through the choice of isotope for the best combination of minimum half-life, minimum retention in the body, and minimum quantity of isotope which will permit detection and accurate measurement. Examples of radioisotopes that can be bound to PlGF antibody and are appropriate for diagnostic imaging include $^{99m}$Tc and $^{111}$In.

The PlGF ligands, antibodies, fusion proteins, and fragments thereof also can be labeled with paramagnetic ions and a variety of radiological contrast agents for purposes of in vivo diagnosis. Contrast agents that are particularly useful for magnetic resonance imaging comprise gadolinium, manganese, dysprosium, lanthanum, or iron ions. Additional agents include chromium, copper, cobalt, nickel, rhenium, europium, terbium, holmium, or neodymium. PlGF ligands, antibodies and fragments thereof can also be conjugated to ultrasound contrast/enhancing agents. For example, one ultrasound contrast agent is a liposome that comprises a humanized PlGF IgG or fragment thereof. Also preferred, the ultrasound contrast agent is a liposome that is gas filled.

In a preferred embodiment, a bispecific antibody can be conjugated to a contrast agent. For example, the bispecific antibody may comprise more than one image-enhancing agent for use in ultrasound imaging. In a preferred embodiment, the contrast agent is a liposome. Preferably, the liposome comprises a bivalent DTPA-peptide covalently attached to the outside surface of the liposome. Still more preferred, the liposome is gas filled.

Imaging Agents and Radioisotopes

In certain embodiments, the claimed peptides or proteins may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$-carbon, $^{51}$chromium, $^{36}$-chlorine, $^{57}$cobalt, $^{58}$cobalt, copper$^{62}$, copper$^{64}$, copper$^{67}$,$^{152}$Eu, fluorine$^{18}$, gallium$^{67}$, gallium$^{68}$, $^{3}$hydrogen, iodine$^{123}$, iodine$^{124}$, iodine$^{125}$, iodine$^{131}$, indium$^{111}$, $^{52}$iron, $^{59}$iron, $^{32}$phosphorus, $^{33}$phosphorus, rhenium$^{186}$, rhenium$^{188}$, Sc$^{47}$, $^{75}$selenium, silver$^{111}$, $^{35}$sulphur, technicium$^{94m}$ technicium$^{99m}$ yttrium$^{86}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as $SNCl_2$, a buffer solution such as sodium-potassium phthalate solution, and the peptide. Intermediary functional groups which are often used to bind radioisotopes which exist as metallic ions to peptides include diethylenetriaminepentaacetic acid (DTPA), DOTA, NOTA, porphyrin chelators and ethylene diaminetetracetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference. These fluorescent labels are preferred for in vitro uses, but may also be of utility in in vivo applications, particularly endoscopic or intravascular detection procedures.

In alternative embodiments, PlGF ligands, antibodies, or other proteins or peptides may be tagged with a fluorescent marker. Non-limiting examples of photodetectable labels include Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1, 3-diazole), Oregon Green 488, *Oregon Green* 500, *Oregon Green* 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red. These and other luminescent labels may be obtained from commercial sources such as Molecular Probes (Eugene, Oreg.).

Chemiluminescent labeling compounds of use may include luminol, isoluminol, an aromatic acridinium ester, an imidazole, an acridinium salt and an oxalate ester, or a bioluminescent compound such as luciferin, luciferase and aequorin. Diagnostic immunoconjugates may be used, for example, in intraoperative, endoscopic, or intravascular tumor or disease diagnosis.

In various embodiments, labels of use may comprise metal nanoparticles. Methods of preparing nanoparticles are known. (See e.g., U.S. Pat. Nos. 6,054,495; 6,127,120; 6,149,868; Lee and Meisel, *J. Phys. Chem.* 86:3391-3395, 1982.) Nanoparticles may also be obtained from commercial sources (e.g., Nanoprobes Inc., Yaphank, N.Y.; Polysciences, Inc., Warrington, Pa.). Modified nanoparticles are available commercially, such as Nanogold® nanoparticles from Nanoprobes, Inc. (Yaphank, N.Y.). Functionalized nanoparticles of use for conjugation to proteins or peptides may be commercially obtained.

Cross-Linkers

In some embodiments, proteins or peptides may be labeled using various cross-linking reagents known in the art, such as homo-bifunctional, hetero-bifunctional and/or photoactivatable cross-linking reagents. Non-limiting examples of such reagents include bisimidates; 1,5-difluoro-2,4-(dinitrobenzene); N-hydroxysuccinimide ester of suberic acid; disuccinimidyl tartarate; dimethyl-3,3'-dithio-bispropionimidate; N-succinimidyl-3-(2-pyridyldithio)propionate; 4-(bromoaminoethyl)-2-nitrophenylazide; and 4-azidoglyoxal. In an exemplary embodiment, a carbodiimide cross-linker, such as DCCD or EDC, may be used to cross-link acidic residues to amino or other groups. Such reagents may be modified to attach various types of labels, such as fluorescent labels.

Bifunctional cross-linking reagents have been extensively used for a variety of purposes. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described (U.S. Pat. No. 5,889,155, incorporated herein by reference). The cross-linking reagents combine a nucleophilic hydrazide residue with an electrophilic maleimide residue, allowing coupling in one example, of aldehydes to free thiols. The cross-linking reagent can be modified to cross-link various functional groups.

Vectors for Cloning, Gene Transfer and Expression

In certain embodiments, expression vectors may be employed to express peptides or proteins, such as fusion proteins, which can then be purified and used. In other embodiments, the expression vectors may be used, for example, in gene therapy. Expression requires that appropriate signals be provided in the vectors, and which include various regulatory elements, such as enhancers/promoters from either viral or mammalian sources that drive expression of the genes of interest in host cells. Elements designed to optimize messenger RNA stability and translatability in host cells also are known.

Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

Where a cDNA insert is employed, typically one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

Selectable Markers

In certain embodiments, the cells containing nucleic acid constructs may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Delivery of Expression Vectors

There are a number of ways in which expression vectors may introduced into cells. In certain embodiments, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, In: *Vectors: A Survey of Molecular Cloning Vectors and Their Uses*, Rodriguez et al., eds., Stoneham: Butterworth, pp. 467-492, 1988; Nicolas and Rubenstein, In: *Vectors: A survey of molecular cloning vectors and their uses*, Rodriguez and Denhardt, eds., Stoneham: Butterworth, pp. 494-513, 1988; Baichwal and Sugden, 1986, *In: Gene Transfer*, Kucherlapati R, ed., New York, Plenum Press, pp. 117-148; Temin, In: *Gene Transfer*, Kucherlapati R, ed., New York, Plenum Press, pp. 149-188, 1986). Preferred gene therapy vectors are generally viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression making them ideally suited for rapid, efficient, heterologous gene expression. Techniques for preeparing replication infective viruses are well known in the art.

In using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

DNA viruses used as gene vectors include the papovaviruses (e.g., simian virus 40, bovine papilloma virus, and polyoma) (Ridgeway, 1988; Baichwal and Sugden, 1986) and adenoviruses (Ridgeway, 1988; Baichwal and Sugden, 1986). One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include, but is not limited to, constructs containing adenovirus sequences sufficient to (a) support packaging of the construct and (b) to express an antisense or a sense polynucleotide that has been cloned therein.

Generation and propagation of adenovirus vectors which are replication deficient depend on a helper cell line, designated 293, which is transformed from human embryonic kidney cells by Ad5 DNA fragments and constitutively expresses E1 proteins (Graham et al., *J. Gen. Virol.,* 36:59-72, 1977). Since the E3 region is dispensable from the adenovirus genome (Jones and Shenk, *Cell,* 13:181-188, 1978), the current adenovirus vectors, with the help of 293 cells, carry foreign DNA in either the E1, the E3, or both regions (Graham and Prevec, *In: Methods in Molecular Biology Gene Transfer and Expression Protocol*, E.J. Murray, ed., Humana Press, Clifton, N.J., 7:109-128, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As discussed, the preferred helper cell line is 293.

Racher et al. (*Biotechnology Techniques,* 9:169-174, 1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) are employed as follows. A cell innoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking is initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking is commenced for another 72 hr.

Other gene transfer vectors may be constructed from retroviruses. The retroviruses are a group of single-stranded RNA viruses characterized by an ability to convert their RNA to double-stranded DNA in infected cells by a process of reverse-transcription (Coffin, In: Virology, Fields et al., eds., Raven Press, New York, pp. 1437-1500, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., *Cell,* 33:153-159, 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., *Virology,* 67:242-248, 1975).

Other viral vectors may be employed as expression constructs. Vectors derived from viruses such as vaccinia virus (Ridgeway, 1988; Baichwal and Sugden, 1986; Coupar et al., Gene, 68:1-10, 1988), adeno-associated virus (AAV) (Ridgeway, 1988; Baichwal and Sugden, 1986; Hermonat and Muzycska, *Proc. Natl. Acad. Sci. USA,* 81:6466-6470, 1984), and herpes viruses may be employed. They offer several attractive features for various mammalian cells (Friedmann, *Science,* 244:1275-1281, 1989; Ridgeway, 1988; Baichwal and Sugden, 1986; Coupar et al., *Gene,* 68:1-10, 1988; Horwich et al., *J. Virol.,* 64:642-650, 1990).

Pharmaceutical Compositions

In some embodiments, a PlGF ligand and/or one or more other therapeutic agents may be administered to a subject, such as a subject with cancer. Such agents may be administered in the form of pharmaceutical compositions. Generally, this will entail preparing compositions that are essentially free of impurities that could be harmful to humans or animals.

One generally will employ appropriate salts and buffers to render therapeutic agents stable and allow for uptake by target cells. Aqueous compositions may comprise an effective amount of a PlGF binding protein or peptide, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the PlGF ligands disclosed herein, its use in therapeutic compositions is contemplated. Supplementary active ingredients also can be incorporated into the compositions.

The methods and compositions claimed herein may include classic pharmaceutical preparations. Administration of these compositions may occur via any common route so long as the target tissue is available via that route. This includes oral, nasal, buccal, rectal, vaginal or topical. Alternatively, administration may be by orthotopic, intradermal, subcutaneous, intramuscular, intraperitoneal, intrathecal, intraarterial or intravenous injection. Such compositions normally would be administered as pharmaceutically acceptable compositions.

The pharmaceutical forms suitable for use include sterile aqueous solutions or dispersions and sterile powders for the preparation of sterile solutions or dispersions. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the compositions can be brought about by the use in the compositions of agents delaying absorption, for example, aluminum monostearate and gelatin.

One skilled in the art would know that a pharmaceutical composition can be administered to a subject by various routes including, for example, orally or parenterally, such as intravenously. In some cases, a PlGF ligand may be displayed on the surface of or incorporated into a liposome. Liposomes consist of phospholipids or other lipids, and are generally nontoxic, physiologically acceptable and metabolizable carriers that are relatively simple to make and administer.

In certain embodiments, an effective amount of a therapeutic agent, such as a PlGF ligand, must be administered to the subject. An "effective amount" is the amount of the agent that produces a desired effect. An effective amount will depend, for example, on the efficacy of the agent and on the intended effect. For example, a lesser amount of an antiangiogenic agent may be required for treatment of a hyperplastic condition, such as macular degeneration or endometriosis, compared to the amount required for cancer therapy in order to reduce or eliminate a solid tumor, or to prevent or reduce its metastasizing. An effective amount of a particular agent for a specific purpose can be determined using methods well known to those in the art.

Therapeutic Agents

Chemotherapeutic Agents

In certain embodiments, chemotherapeutic agents may coadministered with one or more anti-angiogenic agents, such as PlGF ligands. Chemotherapeutic agents include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesylprotein transferase inhibitors, gemcitabine, ifosfamide, mechlorethamine, melphalan, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences", incorporated herein by reference in relevant parts). Some variation in dosage will necessarily occur depending on the condition of the subject being treated. The person responsible for administration will, in any event, determine the appropriate dose for the individual subject.

Hormones

Corticosteroid hormones can increase the effectiveness of other chemotherapy agents, and consequently, they are frequently used in combination treatments. Prednisone and dexamethasone are examples of corticosteroid hormones. Progestins such as hydroxyprogesterone caproate, medroxyprogesterone acetate, and megestrol acetate have been used in cancers of the endometrium and breast. Estrogens such as diethylstilbestrol and ethinyl estradiol have been used in cancers such as breast and prostate. Antiestrogens such as tamoxifen have been used in cancers such as breast. Androgens such as testosterone propionate and fluoxymesterone have also been used in treating breast cancer.

Angiogenic Inhibitors

In certain embodiments, the PlGF ligands disclosed herein may be co-administered with one or more other anti-angiogenic agents, such as angiostatin, baculostatin, canstatin, maspin, anti-VEGF antibodies, anti-vascular growth factor antibodies, anti-Flk-1 antibodies, anti-Flt-1 antibodies, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Immunomodulators

As used herein, the term "immunomodulator" includes cytokines, stem cell growth factors, lymphotoxins and hematopoietic factors, such as interleukins, colony stimulating factors, interferons (e.g., interferons-α, -β and -γ) and the stem cell growth factor designated "S1 factor." Examples of suitable immunomodulator moieties include IL-2, IL-6, IL-10, IL-12, IL-18, IL-21, interferon-gamma, TNF-alpha, and the like.

The term "cytokine" is a generic term for proteins or peptides released by one cell population which act on another cell as intercellular mediators. As used broadly herein, examples of cytokines include lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to a site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines. Similarly, the terms immunomodulator and cytokine overlap in their respective members.

Radioisotope Therapy and Radioimmunotherapy

In some embodiments, the peptides and/or proteins disclosed and claimed herein may be of use in radiionuclide therapy or radioimmunotherapy methods (see, e.g., Govindan et al., 2005, *Technology in Cancer Research & Treatment*, 4:375-91; Sharkey and Goldenberg, 2005, *J. Nucl. Med.* 46:115 S-127S; Goldenberg et al. (submitted MS), "Antibody Pretargeting Advances Cancer Radioimmunodetection and Radioimmunotherapy," each incorporated herein by reference.) In specific embodiments, PlGF ligands may be directly tagged with a radioisotope of use, as discussed below, and administered to a subject. In alternative embodiments, radioisotope(s) may be administered in a pretargeting method as discussed above, using a haptenic peptide or PlGF ligand that is radiolabeled and injected after administration of a bispecific antibody that localizes at the site of elevated PlGF expression in the diseased tissue.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Th, $^{166}$Dy, $^{166}$Ho, $^{186}$Re, $^{189}$Re, $^{189}$Re, $^{212}$Pb, $^{223}$Ra, $^{225}$Ac, $^{59}$Fe, 75Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Ph. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, 1-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

For example, $^{67}$Cu, considered one of the more promising radioisotopes for radioimmunotherapy due to its 61.5 hour half-life and abundant supply of beta particles and gamma rays, can be conjugated to a PlGF ligand such as an anti-PlGF antibody using the chelating agent, p-bromoacetamido-benzyl-tetraethylaminetetraacetic acid (TETA). Alternatively, $^{90}Y$, which emits an energetic beta particle, can be coupled to a peptide, antibody, fusion protein, or fragment thereof, using diethylenetriaminepentaacetic acid (DTPA).

Additional potential radioisotopes include $^{11}C$, $^{13}N$, $^{15}O$, $^{75}Br$, $^{198}Au$, $^{224}Ac$, $^{126}I$, $^{133}I$, $^{77}Br$, $^{113m}In$, $^{95}Ru$, $^{97}Ru$, $^{103}Ru$, $^{105}Ru$, $^{107}Hg$, $^{203}Hg$, $^{121m}Te$, $^{122m}Te$, $^{125m}Te$, $^{165}Tm$, $^{167}Tm$, $^{168}Tm$, $^{197}Pt$, $^{109}Pd$, $^{105}Rh$, $^{142}Pr$, $^{143}Pr$, $^{161}Tb$, $^{166}Ho$, $^{199}Au$, $^{57}Co$, $^{58}Co$, $^{51}Cr$, $^{59}Fe$, $^{75}Se$, $^{201}Tl$, $^{225}Ac$, $^{76}Br$, $^{169}Yb$, and the like.

In another embodiment, a radiosensitizer can be used in combination with a naked or conjugated PlGF ligand, antibody or antibody fragment. For example, the radiosensitizer can be used in combination with a radiolabeled ligand, antibody or antibody fragment. The addition of the radiosensitizer can result in enhanced efficacy when compared to treatment with the radiolabeled ligand, antibody or antibody fragment alone. Radiosensitizers are described in D. M. Goldenberg (ed.), CANCER THERAPY WITH RADIOLABELED ANTIBODIES, CRC Press (1995), which is incorporated herein by reference in its entirety.

The peptide, antibody, antibody fragment, or fusion protein that has a boron addend-loaded carrier for thermal neutron activation therapy will normally be effected in similar ways. However, it will be advantageous to wait until non-targeted immunoconjugate clears before neutron irradiation is performed. Clearance can be accelerated using an antibody that binds to the PlGF ligand. See U.S. Pat. No. 4,624,846 for a description of this general principle. For example, boron addends such as carboranes, can be attached to PlGF ligand antibodies. Carboranes can be prepared with carboxyl functions on pendant side chains, as is well-known in the art. Attachment of carboranes to a carrier, such as aminodextran, can be achieved by activation of the carboxyl groups of the carboranes and condensation with amines on the carrier. The intermediate conjugate is then conjugated to the PlGF antibody. After administration of the PlGF antibody conjugate, a boron addend is activated by thermal neutron irradiation and converted to radioactive atoms which decay by alpha-emission to produce highly toxic, short-range effects.

Kits

Various embodiments may concern kits containing components suitable for treating or diagnosing diseased tissue in a patient. Exemplary kits may contain at least one PlGF ligand. Optionally, other kit ingredients may include one or more other anti-angiogenic agents, chemotherapeutic agents, bi-specific antibodies or other ingredients as discussed above.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more separate containers. In some embodiments, the containers may be vials that contain sterile, lyophilized formulations of a composition that are suitable for reconstitution. A kit may also contain one or more buffers suitable for reconsititution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are included to demonstrate preferred embodiments of the invention. It should be appreciated by those of skill in the art that the techniques disclosed in the examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effects of PlGF on Tumor Cell Growth, Mobility, Angiogenesis and Metastasis

Methods and Materials

Immunohistochemistry, Histopathology and Flow Cytometry

Flow cytometry was performed by standard methods using 1-5 μg/ml primary antibody, and 1:500 dilution of FITC-labeled secondary antibody (Biosource International, Camarillo, Calif.). Data were collected on a BD FACSCalibur flow cytometer (BD Biosciences) using Cell Quest software.

Paraffin-embedded primary breast cancer tissue arrays from US Biomax Inc. (Rockville, Md.) and TARP, NCI (Bethesda, Md.) were stained using standard immunohistochemistry procedures (Taylor et al., 2002a) for PlGF and VEGF expression. Tissue arrays were also probed for Flt-1 or NRP-1 (ABXIS, Seoul, Korea). Slides were deparaffinized, blocked with appropriate normal serum, and incubated with antibodies purchased from Santa Cruz Biotechnology, Inc. (Santa Cruz, Calif.). After incubation with the primary antibody, biotinylated secondary antibody was applied, followed by quenching of endogenous peroxidase in 3% $H_2O_2$. avidin-biotin-horseradish peroxidase (HRP) conjugate was applied to washed slides. Slides were incubated 10 min with HRP substrate, 3,3'-diaminobenzidine tetrahydro-chloride (DAB, from Sigma, St. Louis, Mo.), and counterstained with hematoxylin (Sigma). Stained slides were examined at 100× and rated for intensity of staining by assigning a relative value that reflected the intensity of staining: faint (0.25-0.5), moderate (0.5-1.0), heavy (1.0-2.0), and intense (>2.0); scoring was in 0.25-point increments. All slides were read (blinded) by one researcher, and spot-checked by another.

Only viable-appearing areas of the tumors were assessed, and a value representing the overall intensity and % of cells that were stained was assigned to each slide. Staining of extracellular, connective tissue, and white blood cells was not included in the scores. Background staining (indicated by control Ag8 antibody) was also assessed and then subtracted. Tumor specimens were considered positive if staining intensity was 0.5 or greater. Human tumor xenograft samples were stained with hemotoxylin and eosin.

Cell Lines

To further characterize the cell lines used, MCF-7, MDA-MB-231 and -468 (American Type Culture collection, Mannassas, Va.) were assayed for PlGF or VEGF expression by flow cytometry. MDA-MB-231 and -468, and MCF-7 were also tested for expression of the estradiol receptor alpha (Santa Cruz Biotechnology) by IHC of cell monolayers. MCF-7 was positive, and MDA-MB-231 and -468 were negative for the estrogen receptor. MDA-MB-231 and -468 xenograft tumors were also probed for Flt-1 by IHC, and were positive. No MCF-7 tumors were available for Flt-1 testing.

Isolation and Selection of Phage

A phage library (Ph.D.-12 Phage Display Peptide Library Kit, New England Biolabs, Inc., Ipswich, MA) was panned on recombinant human PlGF-2 (PlGF) or recombinant human VEGF165 (VEGF) (R&D Systems, Flanders, N.J.), according to the supplier's methods. Subsequent panning was performed using either PlGF or a peptide corresponding to the putative receptor-binding site on the PlGF molecule. Phage were submitted to three rounds of panning, and plated out on agar in a series of 10-fold dilutions for titers. Well-isolated plaques were picked from the titer plates and amplified for further investigation.

Sequencing

DNA was isolated from amplified plaques, and sequenced using the primer suggested by the Ph.D. Kit (M13 phage-specific), Thermo Sequenase Radiolabeled Terminator Cycle Sequencing Kit (USB, Swampscott, MA). Binding Peptide 1 (BP1) contained 20 amino acids. A control peptide, CPA, was derived by substituting A for the H, R and D residues in BP1. BP1 and CPA were synthesized commercially (University of Georgia) and investigated in vitro and in vivo.

Peptide sequences were examined for homology to the putative ligand-binding sites on Flt-1 or PlGF. One peptide, Binding Peptide 1 (BPI), had a minor positional homology to the Flt-1 binding site in domain 2, corresponding to Y199 and L204 (Davis-Smyth et al., 1998, *J Biol Chem* 273:3216-3222; Iyer et al., 2001, *J Biol Chem* 276:12153-12161, and its sequence was longer than the others. The other peptides were 9-12 amino acids in length, and were selected based on consistency of sequence between pannings. Two plaque sequences from separate phage were identical (Binding Peptide 3, BP3).

Sequence of Peptides:

| Peptide Name | Sequence |
|---|---|
| BP1 | SHRYRLAIQLHASDSSSSCV (SEQ ID NO: 1) |
| BP2 | QDDHLTTGR (SEQ ID NO: 2) |
| BP3 | QEAFNRLTSRMH (SEQ ID NO: 3) |
| BP4 | RMPYSEHSAPLG (SEQ ID NO: 4) |

Testing of Phage or Free Peptide for Binding to PlGF, VEGF or Flt-1

The protocol suggested by the supplier of the phage display system for panning was used. For each coated well, another well was incubated in buffer (as a buffer control). After removal of the coating solution, plates were blocked in 2% BSA in PBS for 1.5 h at RT. Another uncoated plate was also blocked, and used for diluting the phage. After blocking, amplified phage (~$10^8$ phage/ml) were diluted 1:20 in blocking buffer and 50 μl of each dilution was added to the PlGF-coated/blocked and blocked-only wells. Phage were allowed to bind at RT for 1-2 h. Plates were emptied, and washed by dipping and emptying 3× (wash: 0.05% Tween-20 in PBS). Anti-M13-phage antibody (Amersham Biosciences, Buckinghamshire, England), conjugated to HRP, diluted 1:1000 in blocking buffer, was added to all wells and incubated 1 h at RT. Plates were washed by dipping, as described. The substrate was added, and after 30-60 min, absorbance was read at 410 nm.

Free peptide binding was determined by coating 96-well plates were coated with 10 μg/ml PlGF, 10 μg/ml recombinant human Flt-1 fusion protein (R & D Systems), or 10 μg/ml VEGF. Competition assays were done with 2.5 or 25 U/ml heparin (Sigma, St. Louis, Mo.). BP1, 3, 4, and a scrambled version of BP3 (scrBP3) were synthesized with a linker followed by the FLAG epitope (DYKDDDDK SEQ ID NO:5) at the C-terminus. Thirty minutes after addition of the first reagent, the second reagent was added, followed by another 30 minute incubation. Peptide binding was assessed by probing for the FLAG epitope (Prickett et al., Biotechniques 7:580-9, 1989; Castrucci et al., J. Virol. 66:4647-53, 1992). Absorbance was read at 490 nm. In ELISA-based binding assays, CPA bound PlGF and VEGF, but showed attenuated affinity (50%) for Flt-1. The CPA peptide was consistently inactive in vitro and in vivo.

Tumor Cell Viability

MTT (3-(4,5-dimethylthiazolyl-2)-2,5-diphenyltetrazolium bromide, Sigma) assays were performed under conditions of low serum (1%) to determine PlGF effects on cell viability, the toxicity of the peptides, and their effect on PlGF-mediated breast tumor cell growth (Mosmann, 1983, *J Immunol Meth* 65:55-63; Modrak et al., 2000, Biochem Biophys Res Commun 268:603-606). Peptide concentration was 1-2 μM, and the concentration of exogenous PlGF was 2 nM. The human breast tumor lines tested were: MDA-MB-231, MDA-MB-468 and MCF-7 (ATCC, Mannasses, Va.). Briefly, 96-well plates were seeded with 5-10×$10^4$ cells/ml in medium containing 1% fetal bovine serum (FBS). After 24 h, cells were treated with individual peptides at a concentration of 1-2 μM (4 binding peptides), in quadruplicate, and/or rhuPlGF at a 2-nM concentration. After the designated time points, 0.5 mg/ml MTT (5 mg/ml stock diluted 1:10 in RPMI medium with no serum) was added to the wells (Mosmann, 1983). When purple crystals were clearly visible in the cells, and the plate appeared to be fully developed, the reaction was terminated with acid alcohol (0.04M HCl in isopropanol). Absorbance of the dissolved crystals was read at 570 nm. The 24-h time point was chosen because the in vitro effects of PlGF on tumor cell migration were measurable at this time (see wound-healing assay below). These assays were also performed using medium with 10% FBS, with similar results.

Wound-Healing Assay

To determine the functional effects of PlGF, VEGF and BP peptides on breast tumor and normal human endothelial cells (HECs), wound-healing assays were performed (Verma et al., 2001, *Cell Microbiol* 3:169-180; Sung et al., 2003, *Exp Cell Res* 287:209-218; Itokawa et al., *Mol. Cancer. Ther.* 1:295-302, 2002). MCF-7, MDA-MB-231, and MDA-MB-468 breast tumor cell lines or HECs were seeded onto sterile glass coverslips in Petri dishes or six-well plates. When the cells were 70-80% confluent, the monolayers were scratched with a sterile plastic pipet tip. The coverslips were washed with sterile PBS, and then treated alone or in combinations with PlGF or VEGF (2 nM), peptide (2 μM), or with antibody (0.67 to 1 μg/ml).

Inhibitor concentrations were 50 μM PD98059 (PD98) (mitogen activated protein kinase-kinase 1 [MEK1] inhibitor), 5 nM Wortmannin (phosphatidyl inositol 3 kinase [PI3K] inhibitor), or human recombinant soluble Flt-1 (sFlt-1) (R&D Systems). Peptides or sFlt-1 were incubated with PlGF-, VEGF-containing medium for 10 min before addition to cells. Cells were pre-incubated with PD98 and Wortmannin for 15-30 min before addition of PlGF. Stained (Wright- Giemsa) and mounted coverslips were examined microscopically. Five to ten 100× fields were evaluated by counting the number of cells separated from the wound edges and which appeared to be migrating toward the center of the wound. Results are reported as the average number of cells migrating into the wound/100× field. In some cases data from separate experiments were combined to accommodate inclusion of various treatments in the tables.

Cell Invasion Assays

Cellular invasion was determined by addition of $5\times10^4$ cells to growth factor-reduced Matrigel invasion chambers (BD Biosciences Discovery Labware, Bedford, Mass.) (Taylor et al., 2003b; Passaniti et al., 1992, *Lab Invest* 67, 519-528). Additives to the Matrigel® plugs were pre-incubated together in a total volume of 100 μl PBS at RT for 10 min, after which each additive was added to the Matrigel. Growth factors (2.0 or 0.2 nM), peptide (2 μg/ml), or antibody (1 μg/ml) were added to cells in low serum (0.1% fetal bovine serum [FBS]) medium. Baseline and chemoattractant-based invasion (10% FBS) were included. The number of invading cells was determined by counting the number of cells on the bottom of the invasion chamber membrane after staining at 100× magnification after 24 h (MDA-MB-231) or 48 h (MCF-7, MDA-MB-468). The results of three to five separate experiments are presented.

Effect of Peptide Treatment on Tumor Growth In Vivo

The tissue-culture-grown human breast tumor cell line, MDA-MB-231, was implanted subcutaneously (s.c.) on the flanks of nude mice. When tumors were visible, the mice were weighed and the tumors measured. Treatment with peptides was begun when tumors averaged about 0.06-0.12 $cm^3$ in volume. Mice were treated with 200-μg peptide in PBS by i.p. injection at 3-4-day intervals for 4 weeks. Animals were weighed and the tumors measured at each treatment. In a second experiment, the control peptide, CPA, was included. Three days after the final treatment, tumors and lungs were harvested. Tumor burden of the lungs (from experiment 1) was determined by counting colonies (<20 cells), clusters (>20-100 cells), and nodules (>100 cells) seen in all the lung tissue on a total of 4 slides or sections for each mouse. Data are presented as the average number of each size of metastasis for each treatment group (3-4 mice/group). The total number of each was summed for each treatment group, and divided by the total number of mice in that group. The percent inhibition for metastasis was determined by the formula: % inhibition=(# mock-treated−# treated/# mock-treated)×100.

MDA-MB-231, grown in tissue culture, was also implanted in the mammary fat pad (mfp) of SCID mice ($3\times10^6$ cells, 4-5 mice/group). In this model, large pulmonary metastases are less likely to develop (Richert et al., *Breast Cancer Res.* 7:R819-27, 2005). Peptide treatment was commenced on day 5 after implantation, when small tumors were palpable in all mice (8 treatments). Three days after the final peptide treatment, tumors were removed and weighed. Lungs were harvested and examined microscopically for metastases, as described above.

Statistical Analyses

Binding, viability, motility, angiogenesis, tumor growth, and metastatic tumor burden were evaluated by ANOVA. P<0.05 was considered as significant.

Results

PlGF is Constitutively Expressed in Primary Human Breast Cancer and Breast Tumor Cell Lines The frequency of constitutive PlGF and PlGF-receptor expression by primary breast cancer and breast tumor cell lines was investigated by immunohistochemical staining of tissue arrays, as discussed above. The results, shown in Table 1, demonstrated a higher proportion of PlGF-positive samples than VEGF (43%-60%, PlGF; 13%-14%, VEGF). Expression of the PlGF receptor, NRP-1, was limited to breast cancer parenchyma (27%), but not tumor endothelium. On the other hand, both tumor parenchyma and endothelium were positive for Flt-1 (65% and 56%, respectively).

TABLE 1

Expression of PlGF, VEGF, NRP-1, and Flt-1 by primary breast cancer.

| Marker | Array 1 (%) | Array 2 (%) |
|---|---|---|
| PlGF | 30/69 (43%) | 30/50 (60%) |
| VEGF | 9/70 (13%) | 7/50 (14%) |
| NRP-1 | ND | 25/94 (27%) |
| Flt-1-tumor | ND | 31/48 (65%) |
| Flt-1-vessels | ND | 27/48 (56%) |

# of moderate to strong staining tumors/total # samples/array. Array 1, TARP. Array 2, commercial source. ND, not done Lung carcinomas and brain tumors (glioblastomas) were also among those with relatively high frequency of expression (32% and 20%, respectively, data not shown). Colonic carcinomas were among the lowest constitutive expressers (8%), as were the colonic tumor cell lines (1/4) (not shown).

Human breast cancer cell lines, MCF-7, MDA-MB-231, and MDA-MB-468, were analyzed for PlGF and VEGF expression by flow cytometry. The percent of PlGF-positive cells was 29%, 49%, and 38% for MCF-7, MDA-MB-231, and MDA-MB-468, respectively. The percent of VEGF-positive cells was 8%, 18%, and 13% for MCF-7, MDA-MB-231, and MDA-MB-468, respectively. Thus, these cell lines were relatively high expressers of PlGF and low expressers of VEGF. Both MDA-MB-231 and -468 xenograft tumors express the PlGF receptor, Flt-1. MDA-MB-468 stained faintly for NRP-1 (not shown), and NRP-1 expression by MDA-MB-231 has already been documented (Soker et al., *J. Biol. Chem.* 271:5761-7, 1996). These cell lines were used for subsequent investigation.

Derivation of PlGF-binding Peptides

The relatively high frequency of PlGF, NRP-1, and Flt-1 expression by breast cancer cells suggested that PlGF may have a direct effect on these cells. To investigate the effects of PlGF on breast cancer cells, PlGF- and Flt-1-binding peptides (BPs) were obtained by panning of a phage peptide library. Binding peptides were obtained after at least 3 rounds of panning. Binding peptides 1 and 2 (BP1, BP2) were derived from panning on rhuPlGF, while binding peptides 3 and 4 (BP3, BP4) were derived from phage first panned for two rounds on a peptide corresponding to sequences of the putative receptor-binding site of PlGF, and then on rhuPlGF for the third round. BP3 represents sequences common to two different phage plaques.

After isolation, phage were subjected to an ELISA-based binding assay on PlGF-coated plates. The absorbance readings (410 nm) for the phage BP1, was 0.024 (Phage library background 0.003). The results indicated that binding of the PlGF-panned phage to PlGF-coated wells was 10-20-fold increased over background Peptide BP1 (SHRYRLAIQLHASDSSSSCV SEQ ID NO:1), was synthesized with a C-terminal FLAG epitope, and tested for binding to PlGF and Flt-1, and to VEGF. BP1 bound to PlGF (A490 0.100±0.058) and VEGF165 (A490 0.299±0.174), but most strongly to Flt-1 (A490, 0.886±0.096). Flt-1-binding was further tested by addition of unbound Flt-1 to binding assays where Flt-1 was immobilized. Addition of free Flt-1 (2 nM) caused a 38% decrease in binding of BP1. to immobilized Flt-1 (A490 for 5 μM BP1 only, 0.527±0.025; with added free Flt-1 and BP1, 0.327±0.127).

Additional assays were performed to determine if the presence of PlGF would interfere with the BP1-Flt-1 interaction. PlGF at concentrations between 1 and 100 nM had no significant effect on the binding of BP1 to Flt-1. These findings suggested that BP 1 interacted with a site on Flt-1 other than domain 2, where the major interactions of PlGF with Flt-1 are located. Subsequently, the association of BP1 with the heparin-binding sites present on both Flt-1 and PlGF-2 was investigated. As shown in FIG. 1, addition of heparin to Flt-1-coated plates before addition of BP1 resulted in a 64% decrease in BP1 binding (P<0.0002). However, if BP1 was added prior to addition of heparin, the binding of BP1 was inhibited by only 13% (P>0.05). Thus, BP1 most likely binds to Flt-1 at or near the heparin-binding site.

BP1 may itself contain a heparin binding motif, as the first six residues have the same pattern (XBBXBX) as the first six residues of the heparin binding domain found in vitronectin. This domain may serve as the core of alternative binding peptide sequences that could exhibit increased potency with respect to inhibition of angiogenesis, tumor metastasis and/or tumor cell mobility. The skilled artisan will realize that, for example, randomization of amino acids in the locations indicated as "X" may potentially result in the production of useful analogs of BP1. While the charge distribution may be of significance, substitution of other basic residues (e.g., histidine, arginine, lysine) in the positions indicated as "B" may also result in the production of useful analogs of BP1.

No measurable binding of BP1 to VEGF was detected. Unexpectedly, BP1 also bound to Flt-1 at 10-fold over background. Specificity of the Flt-1 binding was tested by addition of unbound Flt-1 (2 nM) to ELISA-based binding assays, and this caused a 38% decrease in binding of 5 μM BP1 to immobilized Flt-1.

Peptides BP3 and BP4, and a scrambled version of BP3 (BP3scr), also were assayed as free peptides for binding to PlGF and Flt-1, and did not bind detectably to PlGF at concentrations up to 50 M. No measurable binding to Flt-1 was detected for these peptides.

Viability of Breast Tumor Cells when Exposed to PlGF or Peptides

PlGF and all 4 peptides were assayed for their effects on breast tumor cell viability. The cell lines, MCF-7, MDA-MB-231, and MDA-MB-468, were chosen because they typify many primary and metastatic breast cancers. MCF-7 is estrogen receptor-positive and has a moderately well-differentiated histology. MDA-MB-231, originally obtained from a metastatic pleural effusion (Cailleau et al., 1974, *J Natl Cancer Inst* 53:661-674), is estrogen receptor-negative, and forms poorly differentiated grade III adenocarcinoma xenografts. MDA-MB-468 is also estrogen receptor-negative, poorly differentiated, and is tumorigenic in nude mice. All three tumors constitutively produce PlGF 3-4-fold compared to the PlGF-negative colonic tumor cell line, HT-29 (by flow cytometry) and express low levels of the PlGF receptor Flt-1 (data not shown). MDA-MB-231 is the highest producer of PlGF, and MDA-MB-468, the lowest.

Figure 4:
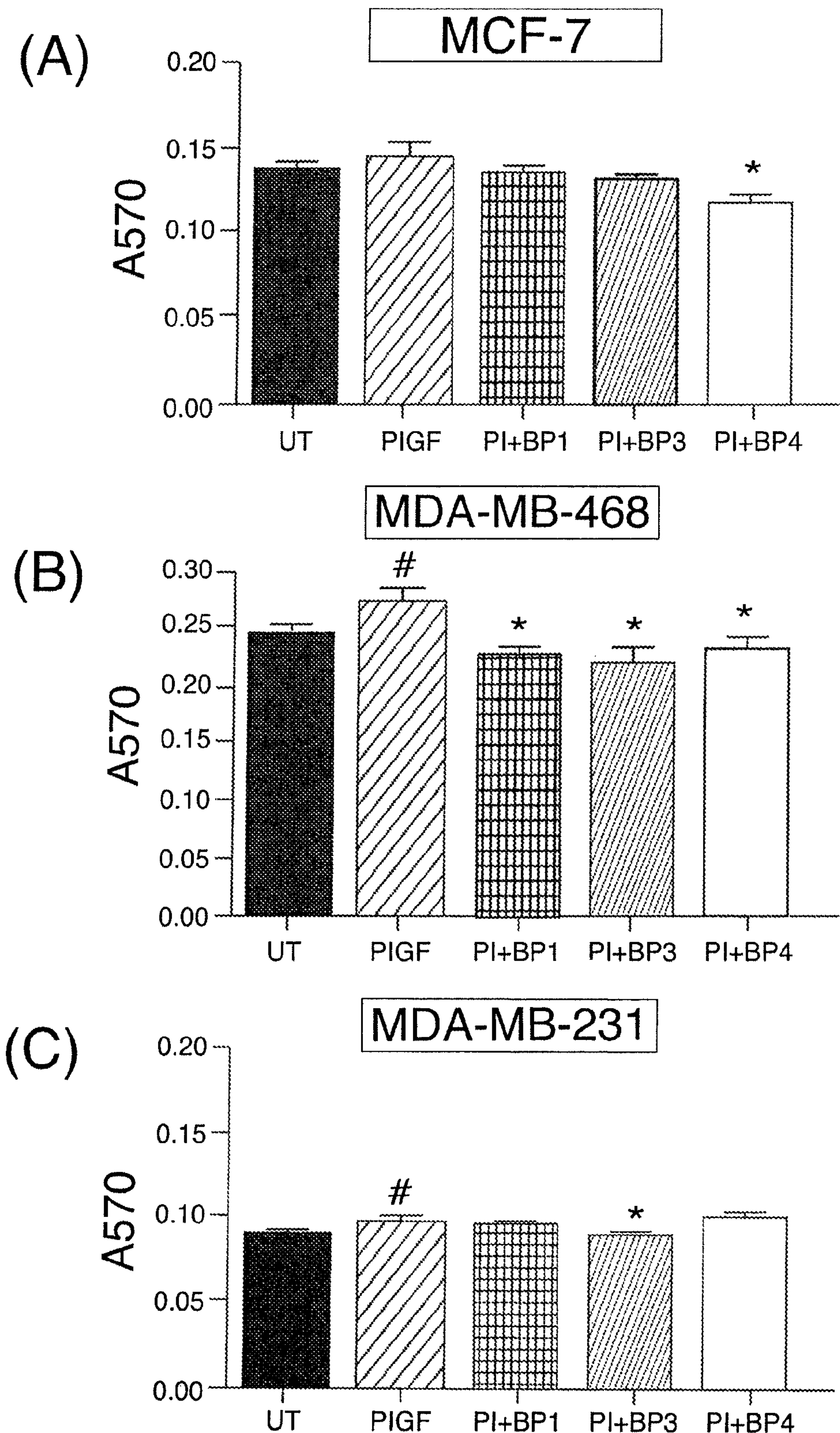
FIG. 4. Exogenous PlGF stimulates increased tumor cell viability. Breast tumor cell lines were treated with PlGF (2 nM) or PlGF and the designated peptides (1-2 μM) under conditions of low serum concentration (1%). Twenty-four hours later viability of the cells was assessed by MTT. # denote $P<0.04$ of PlGF-treated cells compared to untreated controls. Asterisks (*) denote $P<0.03$ compared to PlGF-only (ANOVA).

Addition of PlGF (2 nM) to tumor cell cultures resulted in increased cell numbers after 24 h of culture (P<0.04 for MDA-MB-231 and MDA-MB-468) (FIG. 4). To determine the effect of the peptides on the PlGF-stimulated viability and proliferation, peptides (1-2 μM) were combined with PlGF (2 nM). The results of addition of the peptides to PlGF-containing MTT assays are shown in FIG. 4. Addition of BP4 to PlGF-containing MCF-7 cultures (FIG. 4A) resulted in a significant reduction in cell viability, as did addition of BP3 to MDA-MB-231 (FIG. 4C) (P<0.03). All three peptides decreased the viability of PlGF-containing MDA-MB-468 cultures (FIG. 4B) (P<0.03).

Incubation of tumor cells for 24 h with the peptides alone (2 μM) had no significant effect on cell viability, except for MCF-7 incubated with BP1, where the viability was lowered by 21% (P<0.005). After 48 h of incubation with BP3, MCF-7 also lost viability compared to untreated controls (P>0.05)

PlGF Stimulates Tumor Cell Migration and is Involved in Metastasis

It was determined whether PlGF could increase the likelihood of tumor recurrence or metastasis. Because metastatic tumor cells display increased motility and invasive potential, exogenous PlGF was added to motility and invasion assays containing the breast cancer cell lines, MCF-7, MDA-MB-231, and MDA-MB-468. PlGF caused a 1.8-2.1-fold increase in motility of MDA-MB-231 and MCF-7 (P<0.01), but did not significantly affect the motility of MDA-MB-468. Addition of recombinant soluble Flt-1 (2 nM) significantly blocked the stimulatory effect of PlGF by 55% and 67% for MDA-MB-231 and MCF-7, respectively (P<0.02) (Table 2). Anti-PlGF antibody (1 μg/ml) also blocked the PlGF-mediated motility of MDA-MB-231 and MCF-7 (P<0.02) (Table 2). BP1 also inhibited PlGF-stimulated motility in MDA-MB-231 and MCF-7 significantly (P<0.02). Control peptide, CPA, had no effect, nor did VEGF (2 nM) (Table 2). Anti-VEGF antibody added to PlGF-containing assays did not affect PlGF-stimulated migration of MDA-MB-231, suggesting that the increased motility observed in this cell line was not due to VEGF activity (Table 2).

TABLE 2

PlGF-stimulated tumor cell motility inhibition by peptide BP1, Flt-1, anti-PlGF antibody, anti-VEGF antibody, and PI3K/MEK1 inhibitors.

| Cell line | Growth factor (2 nM) | Test agent | Migrating cells | Relative activity |
|---|---|---|---|---|
| MDA-MB-231 | 0 | 0 | 23.8 ± 6.5 | |
| | PlGF | 0 | 42.0 ± 13.3* | 100 |
| | PlGF | Flt-1 | 19.1 ± 8.0† | 45 |
| | PlGF | BP1 | 13.6 ± 6.1† | 32 |
| | PlGF | CPA | 39.8 ± 10.6 | 106 |
| | PlGF | anti-PlGF | 17.0 ± 6† | 40 |
| | PlGF | anti-VEGF | 34.4 ± 12.6 | 82 |
| | PlGF | PD98059 | 18.4 ± 8.0‡ | 43 |
| | PlGF | Wortmannin | 16.4 ± 5.8‡ | 39 |
| | VEGF | 0 | 11.1 ± 1.8 | 100 |
| | VEGF | BP1 | 14.7 ± 2.1 | 132 |
| | VEGF | CPA | 13.4 ± 4.5 | 121 |
| | VEGF | anti-VEGF | 11.5 ± 2.3 | 104 |
| | VEGF | anti-PlGF | 13.8 ± 14.6 | 124 |
| MDA-MB-468 | 0 | 0 | 13.4 ± 9.1 | |
| | PlGF | 0 | 14.7 ± 9.8 | 100 |
| | PlGF | Flt-1 | 7.8 ± 5.9† | 53 |
| | PlGF | BP1 | 14.3 ± 8.1 | 97 |
| | PlGF | CPA | 21.6 ± 6.1 | 147 |
| | PlGF | anti-PlGF | 7.6 ± 5.7† | 52 |
| | VEGF | 0 | 14.0 ± 11.3 | 100 |
| | VEGF | BP1 | 15.8 ± 9.5 | 113 |
| | VEGF | CPA | 14.6 ± 8.0 | 104 |
| | VEGF | anti-VEGF | 14.2 ± 11.5 | 101 |
| MCF-7 | 0 | 0 | 12.2 ± 11.4 | |
| | PlGF | 0 | 22.1 ± 13.4* | 100 |
| | PlGF | Flt-1 | 10.4 ± 8.2† | 47 |
| | PlGF | BP1 | 10.2 ± 7.8† | 45 |
| | PlGF | anti-PlGF | 10.9 ± 4.9† | 49 |
| | VEGF | 0 | 12.7 ± 4.1 | 100 |
| | VEGF | BP1 | 12.9 ± 2.9 | 102 |
| | VEGF | CPA | 19.4 ± 8.9 | 111 |
| | VEGF | anti-VEGF | 12.9 ± 4.3 | 102 |

PlGF, VEGF and Flt-1, 2 nM; peptide, 2 μM. Antibody concentration was 1 μg/ml. MEK1 inhibitor, PD98059 (PD98), 50 μM. PI3K inhibitor, Wortmannin, 5 nM. Results are presented as average number of cells migrating into the 'wound'±SD from 5-10-100× microscopic fields/treatment/experiment at 18-24 h. n=2-4 experiments. Values for antibody and inhibitor treatments were from separate experiments which included all relevant controls. In two experiments all values were approximately one half of those in the majority of previous experiments, and so they were normalized by a factor of 2, and then averaged with other experiments. UT denotes untreated controls. * P<0.01 (ANOVA) compared to UT; t P<0.02 (ANOVA) compared to PlGF only. ‡P<0.001 (ANOVA) compared to PlGF only. Relative activity was determined by dividing the average value for the treatments by the PlGF- or VEGF-only value.

Both PI3K and MEK1 activation are often linked to tyrosine kinase receptor (RTK) intracellular signaling. In addition, active PI3K and MEK1 have been implicated in tumor cell migration (Zeng et al., *J. Biol. Chem.* 276: 26969-79, 2001; Hollande et al., *Am. J. Physiol. Gastrointest. Liver Physiol.* 280:G910-21, 2001). To investigate whether PlGF-stimulated motility was due to activation of either of these kinases, MDA-MB-231 was treated with PlGF and inhibitors of PI3K (Wortmannin, 5 nM) or MEK1 (PD98059, 50 μM [PD98]). PD98 and Wortmannin significantly inhibited PlGF-stimulated migration by 68% and 72%, respectively (P<0.001) (Table 2). These results suggest that PlGF stimulates cellular motility through the activation of the PI3K and MEK1 pathways, possibly through the activation of PI3K by Flt-1.

Figure 2:
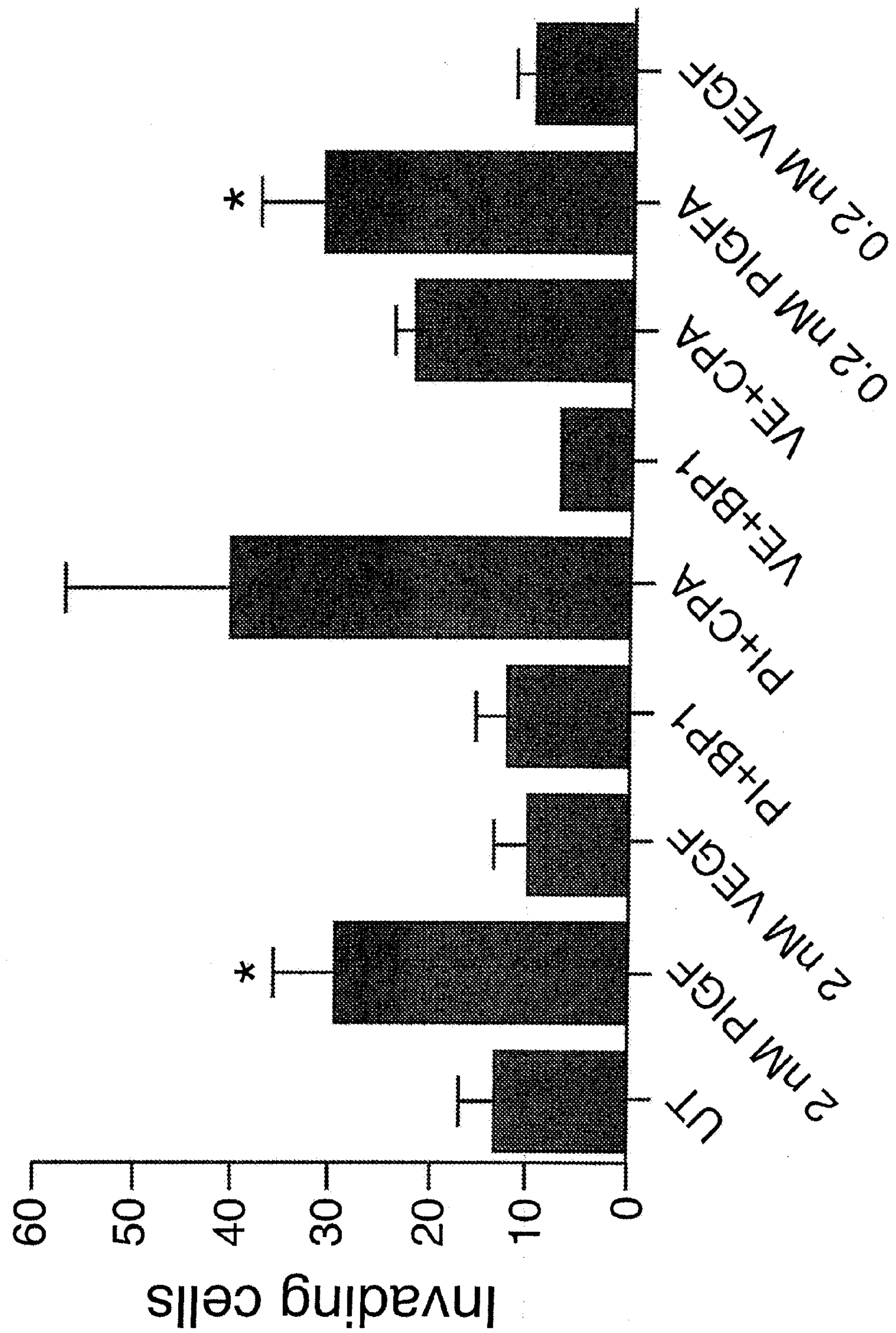
FIG. 2. PlGF stimulates in vitro invasion of MDA-MB-231 cells. The graph represents the cumulative results±SD (n=3-5 experiments). Abbreviations used in the graph: 'Pl' is PlGF; 'VE' is VEGF. * $P<0.05$ (ANOVA).

Because the ability to invade the basement membrane is essential for metastasis, invasion assays with added PlGF or VEGF were performed. Addition of PlGF at both 2.0 and 0.2 nM resulted in nearly 3-fold increased invasion of MDA-MB-231 after 24 h (11±8.1 untreated vs. 30±13.7 (2.0 nM) or 28±12 (0.2 nM) PlGF-treated, P<0.05) (FIG. 2). VEGF (2.0 nM or 0.2 nM) did not alter the invasion capacity of MDA-MB-231 (10±8.0 cells). Addition of peptide BP1 resulted in a 50% decrease in PlGF-stimulated invasion (15±4.2 cells) (P<0.02 vs. PlGF-only). The control peptide, CPA, did not inhibit the activity of PlGF (35±17.3 cells). Addition of anti-PlGF antibody (0.6 μg/ml) to the 0.2 nM PlGF assays resulted in a 46% reduction in invasive cells (15±2.3 cells, one experiment). Taken together, these results suggest that PlGF stimulates invasiveness in the aggressive tumor cell line, MDA-MB-231, and that the inhibitory peptide, BP1, similar to the PlGF antibody, inhibits this activity. Similar results were obtained for MDA-MB-468 and MCF-7, but were not statistically significant (Table 3).

TABLE 3

PlGF increases invasion potential of breast cancer cell lines. BP1 inhibits PlGF-mediated invasive potential.

| Line | Untreated | PlGF | PlGF + BP1 | PlGF + CPA | BP1 |
|---|---|---|---|---|---|
| MCF-7 | 1 | 2.1 ± 0.7 | 0.3 ± 0.0 | 1.0 ± 0.6 | 0.7 ± 0.4 |
| MDA-MB-231 | 1 | 4.0 ± 2.2* | 1.3 ± 0.1† | 4.9 ± 2.4 | 1.0 ± 0.6 |
| MDA-MB-468 | 1 | 1.8 ± 0.3 | 0.6 ± 0.4 | 1.2 ± 0.7 | 1.2 ± 0.3 |

Average fold-change in the number of cells on the membrane after 24 h (MDA-MB-231) or 48 h (MDA-MB-468 and MCF-7) compared to untreated controls ± SD. Concentration of PlGF, 0.2 nM; peptide, 2 μg/ml. n = 2-4 experiments/cell line.
*P < 0.01 vs. Untreated.
†P < 0.02 vs. PlGF-only.

Figure 3:
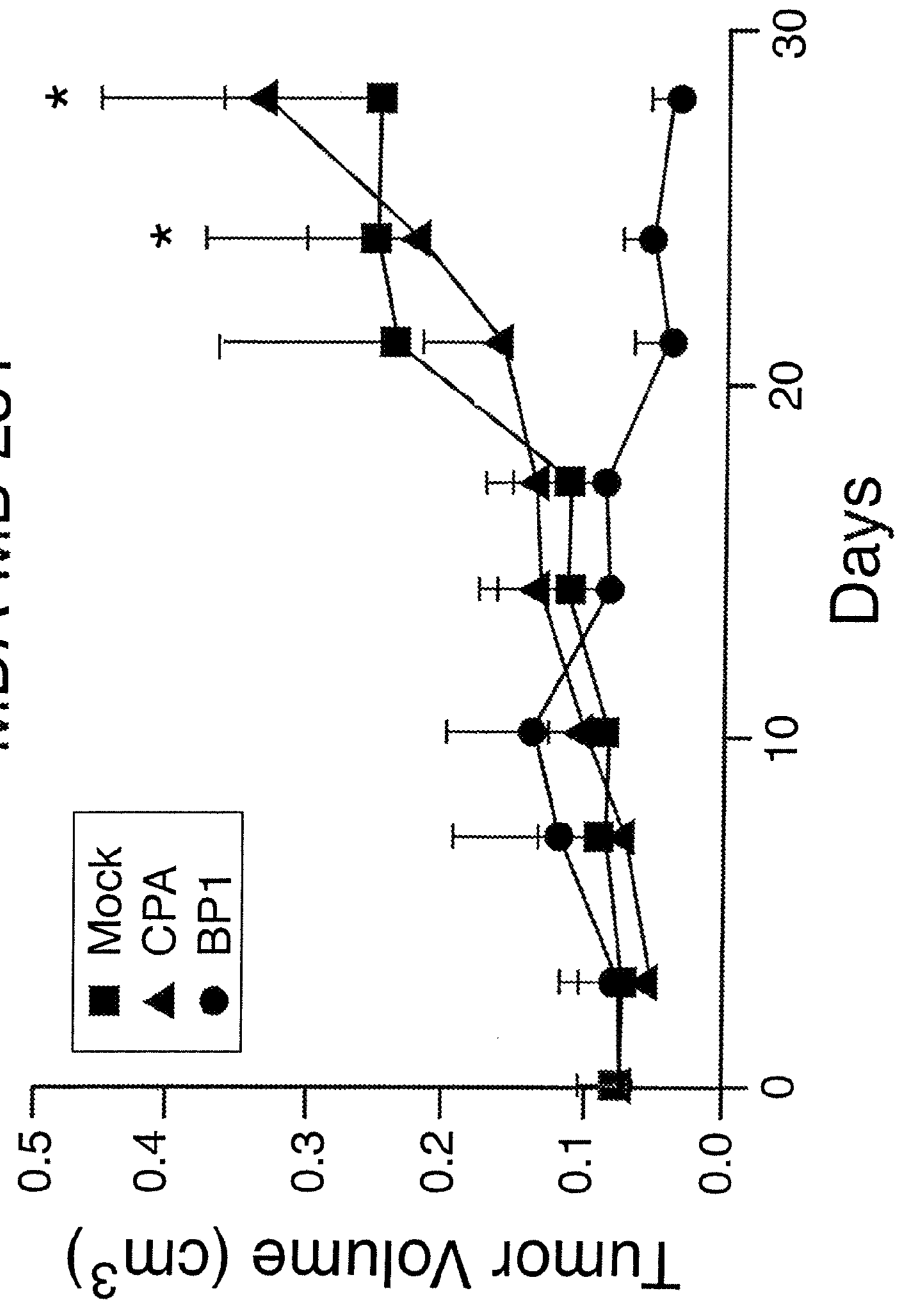
FIG. 3. BP1 inhibits MDA-MB-231 xenograft growth and metastasis. Tumor volume vs. time, s.c. model. Results shown are from one of two experiments±SD (n=3-4 mice/treatment). *$P<0.05$ vs. mock-treated or CPA (change in tumor volume (ANOVA)).

To test for therapeutic activity of the peptide, BP1, mice were implanted with human breast cancer cells, MDA-MB-231, which produces lung metastases spontaneously when implanted as a subcutaneous tumor. When the tumors averaged 0.12 $cm^3$ in volume, either mock-treatment or therapy with BP1 was initiated at 200 μg, two times per week for 4 weeks. Mice receiving BP1 showed a 37% reduction in tumor size compared to mock-treated controls. In a subsequent experiment, treatment was commenced when tumors were 0.07-0.08 $cm^3$. After 4 weeks of treatment, as described, the mean volume of the mock- and CPA-treated tumors was 0.25 and 0.33 $cm^3$, respectively, whereas BP1-treated tumors averaged 0.04 $cm^3$ (P<0.05 BP1 vs. mock- or CPA-treated tumors) (FIG. 3).

Three days after treatment, primary tumors and lungs were removed for microscopic examination. Typically, the lungs of mock-treated animals contained multiple large and small metastases, with many foci of tumor growth mostly surrounding the lung blood vessels, with spread into the surrounding parenchyma (not shown). The lungs of mock-treated controls averaged 78±25 nodules, 76±19 clusters, and 36±6 colonies/total lung tissue/mouse. In contrast, the BP1-treated lungs averaged 5±2, 9±2, and 5±2 nodules, clusters, and colonies, respectively, per mouse. This constituted a 94% decrease in the number of metastatic lung nodules in the peptide-treated animals (P<0.007).

In an orthotopic mammary fat pad (mfp) model using MDA-MB-231, treatment with BP1 decreased tumor weight by 23% (mock-treated, 0.423±0.089 g; CPA, 0.416±0.083 g; BP1, 0.345±0.095), which did not reach statistical significance. The mfp-implanted MDA-MB-231 did not produce large lung nodules, possibly due to the short duration of the experiment (4.5 weeks). However, micrometastases (20 to >100 cells) were apparent adjacent to pulmonary veins (not shown). Micrometastasis counts were 3.4±1.9, 2.8±1.3, and 0.6±0.5 per mouse for mock-treated, CPA, and BP1, respectively (P<0.02 vs. mock or CPA-treated), a reduction in metastases of 82%.

Figure 5:
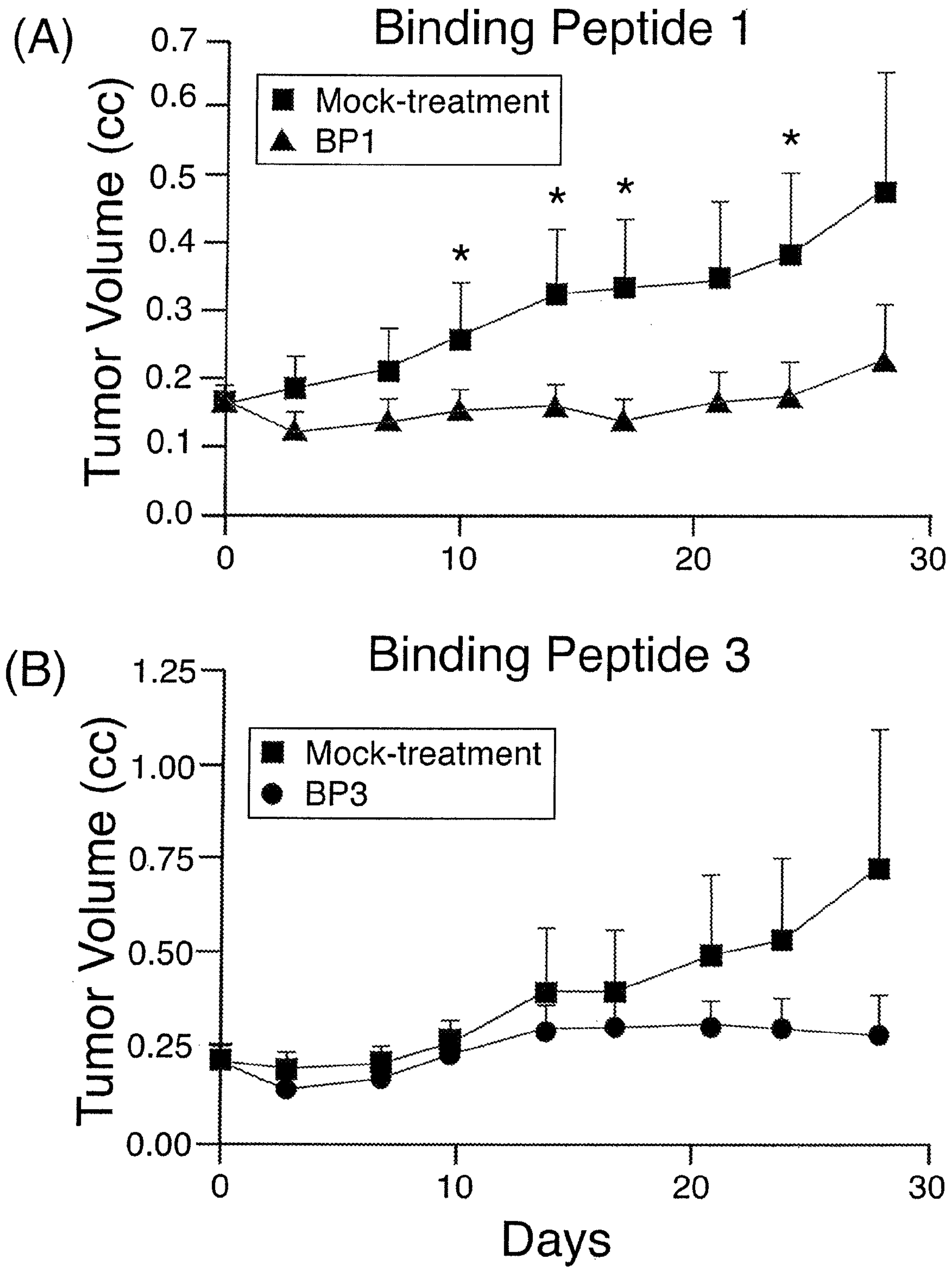
FIG. 5. Treatment of mice bearing MDA-MB-468 xenografts with peptides BP1 or BP3. Mice were treated every 3-4 days with 200 ug BP as described in Methods. Tumor volume was measured 2×/week. * $P<0.05$ at days 10, 14, 17 and 24 (change in tumor volume (ANOVA)).

Mice bearing MDA-MB-468 xenografts (average tumor volume: 0.19 $cm^3$) were treated with i.p. injections of individual peptides (200 μg/dose) (FIG. 5). After 4 weeks of twice-weekly treatment, tumor growth was inhibited by 49% and 58% in mice treated with BP1 (FIG. 5A) or BP3 (FIG. 5B), respectively. The effect of BP3 on tumor growth was apparent after 2 weeks of treatment (FIG. 5B), whereas the inhibitory effect of BP1 was evident after one week (FIG. 5A). The average changes in individual tumor volumes during treatment with BP1 were significant (P<0.05) at days 10, 14, 17 and 24 (FIG. 5A). Treatment with BP2 was ineffective; tumors continued to grow at almost the same rate as the mock-treated controls (results not shown). BP4 treatment produced a 20% inhibition of tumor growth (results not shown).

Inhibition of Angiogenesis

To further investigate the effect of PlGF binding peptides on endothelial cell migration and angiogenesis, Matrigel basement membrane plugs containing PlGF, BP1, BP2, or PBS were implanted s.c. on the flanks of nude mice. The number of interior microvessels in the PBS controls was 16.2±11.4/$mm^2$. PlGF-only implants contained 28.9±17.2/$mm^2$ (1.8-fold vs. mock-treated implants), and implants with PlGF and BP1 contained only 12.3±13.0 microvessels/$mm^2$ (P<0.02).

Discussion

Several studies have indicated that PlGF expression by cancers, including breast, correlates with recurrence, metastasis and mortality (Wei et al., Gut 54:666-72, 2005; Chen et al., Cancer Lett. 213:73-82, 2004; Parr et al., Eur. J. Cancer 41:2819-27, 2005; Weidner et al., Am. J. Pathol. 143: 401-9, 1993; Zhang et al., World J. Surg. Oncol. 3:68, 2005). PlGF is also associated with a number of pathological states (Carmeliet et al., Nat. Med. 7:575-83, 2001) and tumor neovascularization (Li et al., FASEB J. 20:1495-97, 2006; Taylor et al., Int. J. Cancer 1-5:158-69, 2003).

Clinical studies of VEGF and PlGF in human cancer are conflicting. For instance, in one report, PlGF, rather than VEGF, stimulated growth of Philadelphia chromosome-positive acute myelogenous leukemias ex vivo (Ikai et al., Eur. J. Haematol. 75:273-9, 2005). On the other hand, VEGF was associated with renal cell cancer stage, histological grade, as well as its vascularity and venous invasion (Matsumoto et al. Anticancer Res. 23:4953-8, 2003). These authors reported that PlGF also was an independent prognostic factor for this cancer.

Multiple anti-VEGF agents have been developed, and some, including blocking antibodies, small molecules that prevent VEGF-receptor binding, and anti-sense oligonucleotides, have been tested in clinical trials (Whatmore et al., 2002, Angiogenesis 5:45-51; Mulligan-Kehoe et al., 2002*, J Biol Chem* 277:49077-49089; Shi and Siemann, 2002*, Br J Cancer* 87:119-126; Yang et al., 2003*, NEJM* 349, 427-434). The results of these studies suggest that tumor angiogenesis is complex and redundant; i.e., that there may be 'back-up' mechanisms that establish a blood supply to malignancies when VEGF is diminished by treatment, or in tumor types with low VEGF expression. PlGF is likely to be involved in this functional redundancy. PlGF is also arteriogenic, causing the formation of arteries from pre-existing anastomoses (Pipp et al., 2003).

The data presented above show that PlGF enhances the metastatic potential of breast cancer cells, because it stimulates motility and invasiveness, which are associated with the epithelial-to-mesenchymal transformation that characterizes metastasis in tumors. In contrast, exogenously added VEGF had no effect on tumor cell motility or invasiveness in these assays. These results differ from those of Bachelder et al. (Cancer Res. 62:7203-6, 2002), where VEGF was found to be a stimulator of invasion (MDA-MB-231). However, this study did not include PlGF; therefore, comparisons of the growth factors cannot be made. Our results are based on the presence of PlGF or VEGF in the tumor cell environment, whereas Bachelder et al. (2002) used RNAi to suppress VEGF production by the cells, the results of which may differ from VEGF's paracrine effects.

Another report documented an inhibitory role for PlGF when it is overexpressed by tumor lines that are normally low-PlGF and high-VEGF expressers (Xu et al., Cancer Res. 6:3971-7, 2006. This pattern of expression differs from that of the breast lines used in the present study, which were high-PlGF, low-VEGF expressers, a pattern that mimics primary human breast carcinomas. At least one other study showed that VEGF and PlGF synergize to stimulate angiogenesis in pathological conditions (Carmeliet et al., 2001). The contribution of PlGF or VEGF to tumor pathology is most likely complex, and may in part be due to their relative abundance in the tumor microenvironment, as well as the presence of their active receptors on tumor cells and endothelium.

As disclosed herein, the capacity of PlGF to stimulate cancer cell motility and invasion was inhibited with anti-PlGF antibody, as well as with BP1, the PlGF-2/Flt-1 antagonistic peptide developed. It could be surmised that if PlGF were inhibitory, then its removal would allow VEGF-mediated activity to proceed, which was not the case.

Potential intracellular mechanisms for the stimulatory effect of exogenous PlGF were investigated, and the results showed that the PI3K and MEK1 pathways likely participate in PlGF-stimulated migration. These pathways have been linked previously to cell migration (Hollande et al., 2001), but these kinases also participate in other processes that promote cancer progression, including translation of proteins, gene regulation, proliferation, invasion, and resistance to apoptosis (Zeng et al., J. Biol. Chem. 276: 26969-79, 2001; Hollaned et al., 2001; Belka et al., Int. J. Radiat. Oncol. Biol. Phys. 58:542-54, 2004; Pommery et al. Ann. Pharm. Fr. 63:69-75, 2005; Bancroft et al., Clin. Cancer Res. 7:435-42, 2001; Mekhail et al., Cell Cycle 3:1027-9, 2004; Pollheimer et al., Angiogenesis 3:159-66, 1999). PlGF-expressing tumor cells may obtain survival benefits through autocrine/paracrine pathways that render them more resistant to death signals and which allow them to migrate toward a blood supply when needed.

In order to elucidate the role of PlGF in tumor and endothelial cell biology, we developed an antagonistic peptide, BP1, which inhibited the activity of PlGF on both tumor and endothelial cells, and affected spontaneous metastasis in vivo. The results herein indicate that BP1 antagonizes PlGF-2/Flt-1-heparin associations. Heparin-binding is essential for the full activation of some receptor tyrosine kinases (Park et al., Bioechem. Biophys. Res. Comm. 264:730-4, 1999; Schlessinger et al. Molec. Cell. 6:743-50, 2000; Ito et la., Angiogenesis 3:159-66, 1999), which is supported by our observation that inhibition of PI3K and MEK1 pathways often linked with receptor tyrosine kinases, such as Flt-1, prevented cell migration stimulated by PlGF. By preventing the close association of heparin with PlGF-2 and Flt-1, BP1 may prevent the transmission of activation signals to the interior of the cell.

Crystallization studies of the FGF-FGFR-heparin complex document that heparin makes multiple contacts with both the ligand and the receptor. This association enhances dimerization of the receptor, which is necessary for activation (Park and Lee, 1999; Schlessinger et al., 2000; Ito and Claesson-Welsh, 1999, Angiogenesis 3:159-166). By interfering with this complex, BP1 may prevent this close association of heparin with PlGF and Flt-1. We have found that exogenous heparin included in angiogenesis assays augments the formation of vessels even in the absence of added growth factors, such as VEGF or PlGF (unpublished data). In this case, the increased angiogenesis is most likely due to heparin-mediated enhancement of interactions between growth factors endogenous to the Matrigel and receptors on cells migrating into the implants.

In addition to inhibiting PlGF-mediated migration, BP1 was able to inhibit the growth of microvessels in PlGF-loaded basement membrane implants. This inhibition of endothelial cell migration and the establishment of vessels in tumors, taken together with the migration assay data, suggest that the function of PlGF in breast cancer pathology is to stimulate endothelial cell migration and, possibly, tube formation (data not shown), and to also cause movement of tumor cells themselves toward the blood supply.

Bae et al. (Clin. Cancer Res. 11:2651-61, 2005) recently reported the anti-cancer potential of a Flt-1 antagonistic peptide that inhibited VEGF binding to Flt-1, as well as the growth and metastasis of VEGF-secreting colon tumor xenografts. The activity of this peptide was determined by its interaction with endothelial cells, using VEGF as the stimulator of migration and proliferation, rather than tumor cells. It is interesting that the peptide used by these authors also inhibited the binding of PlGF to Flt-1, and part of its efficacy may stem from this interaction. Their peptide, however, appears to differ from BP1, because it interferes with the Flt-1 domain-2 growth factor binding site (Bae et al., 2005), with no evidence of interaction with the heparin-binding domain. Thus, the peptide presented by Bae et al. most likely functions differently than BP1.

The in vivo role of PlGF in cancer was studied by treating human breast cancer xenografts that spontaneously metastasize with BP1. Treatment with the BP1 peptide arrested s.c. MDA-MB-231 tumor growth and decreased the occurrence of pulmonary metastases by 94%, and by 82% in an orthotopic (mfp) model. These results demonstrate the growth- and metastasis-inhibiting properties of anti-Flt-1 peptides, such as BP1, indicating that this receptor may play a key role in the progression of certain cancers, and represents a target for anticancer therapy.

In summary, we have demonstrated increased expression of PlGF in some primary human cancers and cell lines, especially breast cancer. PlGF increased the proliferation of breast cancer cell lines, MDA-MB-231 and -468, and the motility of MCF-7 and MDA-MB-231. To our knowledge, this is the first report documenting the direct activation of malignant cells by PlGF. Further, we have isolated a peptide, BP1, that binds both PlGF and Flt-1 and which ultimately disrupts the activity of the PlGF-2/Flt-1 ligand receptor pair in vitro. The activities blocked by BP1 include PlGF-stimulated tumor cell viability and motility, as well as the formation of microvessels in basement membrane implants. In addition, treatment of tumor-bearing mice with peptide BP1 inhibited the s.c. growth of the breast tumor xenograft, MDA-MB-468, and markedly reduced the establishment of lung metastases by MDA-MB-231.

Example 2

Inhibition of PlGF Mediated Angiogenesis in a Mouse Corneal Assay

The ability of PlGF ligands to block PlGF—mediated angiogenesis in corneal tissues in vivo is investigated. Corneal micropockets are created using a modified von Graefe cataract knife in both eyes of male 5-6-wk-old C57B16/J mice. Micropellets comprised of a sustained release formulation of polyglucuronic acid/polylactic acid containing 100 ng of PlGF or PlGF with 1 μM BP-1, BP-2, BP-3 or BP-4 are implanted into each corneal pocket. Eyes are examined by a slit-lamp biomicroscope on day 5 after pellet implantation. Vessel length and neovascularization are measured.

PlGF induces a strong angiogenic response with formation of a high density of microvessels. Addition of BP-1, BP-3 or BP-4 inhibits PlGF mediated angiogenesis in corneal tissues. Treatment of a subject of diabetic retinopathy or macular degeneration results in an inhibition of blood vessel formation and ameliorates the condition.

Example 3

BP1 Fusion Proteins and Conjugates

For purposes of oral administration or in other embodiments, BP1 and its analogs may be recombinantly or chemically linked to a carrier protein. For linking peptides composed of the 20 common L-amino acids found in naturally occurring proteins, recombinant DNA methods are preferred. For linking peptide mimetics or peptides that contain D-amino acids, modified amino acids, or unnatural amino acids, only chemical conjugation methods are currently feasible. As disclosed herein, a general method of preparing conjugates of BP1 linked to the carbohydrates of the Fc of human IgG1 (hFc) is provided. Methods of constructing three exemplary fusion proteins comprised of BP1 and hFc are disclosed below.

Figure 6:
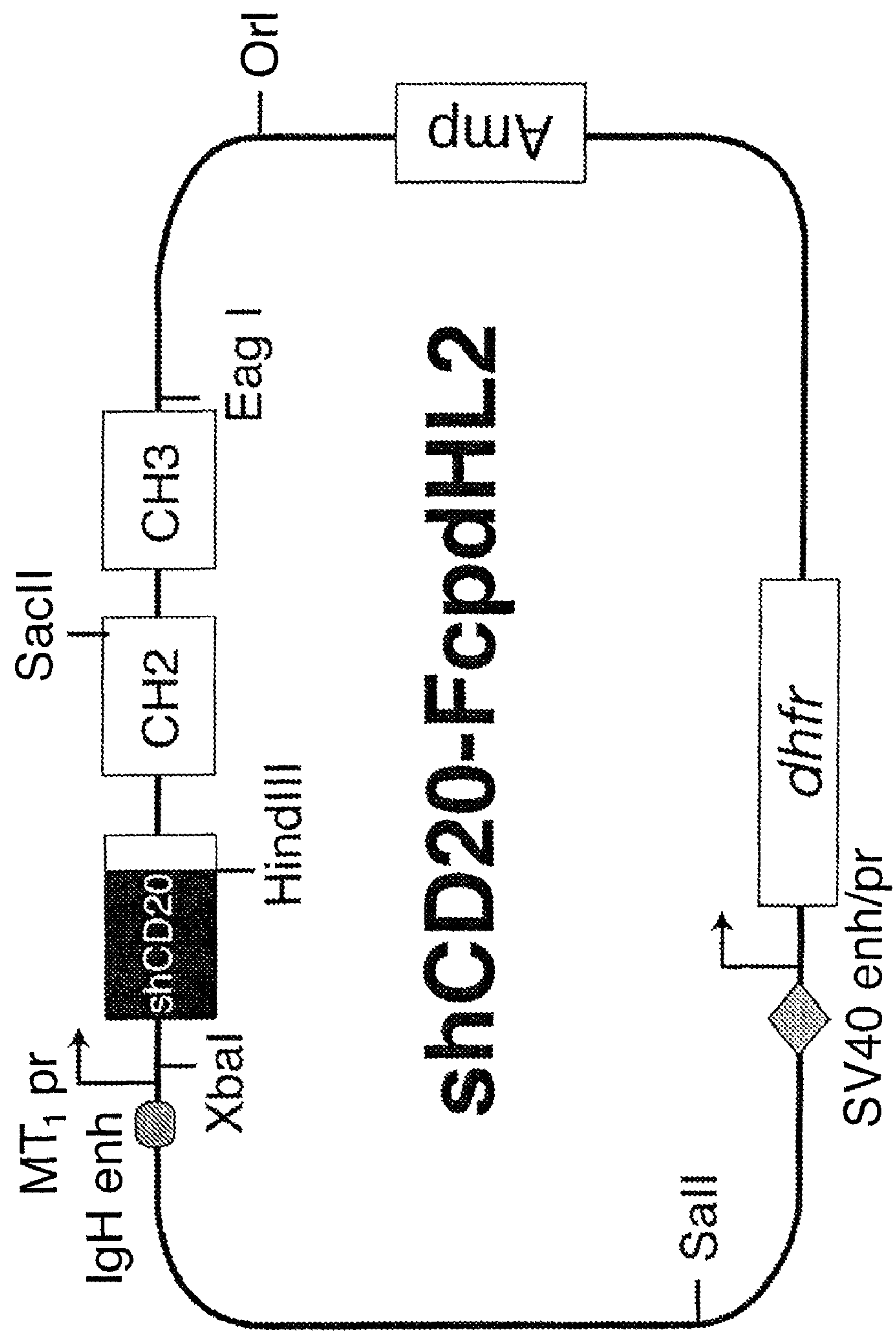
FIG. 6 Expression vector for hFc. The Figure provides a schematic diagram of an exemplary vector (pdHL2-sCD20-hFc) that serves as the template for constructing a vector (pdHL2-hFC) for expressing hFc. The recombinant hFc may be chemically conjugated to BP1 as described in Example 4 or fused to hFc as described in Example 5.

A vector for expressing hFc in myeloma cells is prepared using standard recombinant DNA techniques. The expression vector shCD20-Fc-pdHL2 (FIG. 6) is used as the DNA template to amplify the coding sequences for Fc (hinge, CH2, and CH3 domains) by PCR. Two PCRs are performed. The first PCR is to amplify the entire leader peptide sequence (fragment A) using the pair of primers shown below.

```
5' Xba I:
TCTAGAGCACACAGGACCTC      (SEQ ID NO: 6)

3' Hind3:
GAAGCTTGGAGTGGACACCT      (SEQ ID NO: 7)
```

The second PCR is to amplify hinge and CH2 (fragment B) using the pair of primers shown below:

```
5' Hind3:
AAGCTTCCGACAAAACTCAC      (SEQ ID NO: 8)

3' Sac2:
CCGCGGCTTTGTCTTGGCAT      (SEQ ID NO: 9)
```

Following digestion of shCD20-Fc-pdHL2 with XbaI and Sac2, the larger DNA fragment is ligated to fragments A and B to obtain the expression vector for Fc (hFc-pdHL2).

Example 4

Conjugating BP1 to hFc

Myeloma cells are transfected with hFc-pdHL2 and screened for positive clones. The highest producer is grown in roller bottles and the culture supernatant is purified on Protein A to obtain hFc. Conjugation of BP1 to hFc is performed using one of the two methods described below. In the first method, hFc is oxidized by sodium periodate to generate aldehyde groups in the carbohydrates. Following a desalting step, the oxidized hFc is derivatized with a hetero-crosslinker such as BMPH (Pierce, Product # 22297) to introduce maleimide groups via the reaction of hydrazide with aldehyde. Following removal of excess reagents, the maleimide-coupled hFc is conjugated to BP1 via the reaction of the cysteine residue in BP1. An alternative method is to couple BMPH to BP1, isolate the resulting product using reversed-phase HPLC, and react BMPH-BP1 with oxidized hFc.

Example 5

Expression Vector for BP1-hFc

In alternative embodiments, BP1-hFc is constructed as a fusion protein composed of two identical polypeptides, each composed of BP1 linked to the hinge, CH2 and CH3 of human IgG1 via a flexible linker, such as $(GGGGS)_3$. The two polypeptides are covalently associated by two disulfide bonds formed from the cysteine residues in the hinge. BP1-Fc is expected to confer the following advantages: (1) the affinity of BP1 for the heparin binding domain of VEGFR1 would be enhanced due to bivalent BP1; (2) the increase in molecular size (≈60 kDa) could better exclude heparin from binding to VEGFR1, resulting in a more efficient inhibition of the interaction between PlGF and VEGFR1; and (3) the presence of Fc would prolong the serum half life and enable oral or pulmonary delivery by binding to the neonatal Fc receptor (FcRn) expressed in epithelial cells.

A vector for expressing BP1-Fc in myeloma cells is constructed as follows. Briefly, three long oligonucleotides are synthesized with 10-15 by overlap to cover the 114 by sequence encoding BP1 and the (GGGGS)3 linker, with HindIII sites added at the ends. The oligonucleotides are annealed and extended with DNA polymerase. The resulting DNA fragment containing BP1 and the linker is purified and cloned into an intermediate vector, followed by sequencing confirmation. The fragment is then isolated by digesting the intermediate vector with HindIII, and cloned into HindIII-cut Fc-pdHL2 (see Example 3). Since there are 2 possible orientations, the correct one is identified by double enzyme digestion and isolated (BP1-hFc-pdHL2)

Myeloma cells are transfected withBP1-hFc-pdHL2 and selected for high producing clones. The highest producer is grown in roller bottles and the culture supernatant is purified on Protein A to obtain BP1-hFc.

Example 6

Dimeric BP1-hFc (BP1-hFc-ddd2)

A fusion protein composed of dimeric BP1-hFc is obtained by appending a specific peptide sequence termed ddd2 (SEQ ID NO:10) to the C-terminus of BP1-hFc. The dimeric BP1-hFc is stabilized by disulfide bonds and contains four BP1.

```
ddd2
                                        (SEQ ID NO: 10)
MCGHIQIPPGLTELLQGYTVEVLRQQPPDLVEFAVEYFTRLREARA
```

Example 7

BP1-hFc×anti-VEGFR2Fab (~160 kDa)

BP1-Fc is linked by disulfide bond to anti-VEGFR2Fab using the A2B technology to generate a conjugate of ~160 kDa capable of targeting both VEGFR1 and VEGFR2. The B-form of anti-VEGFR2 is first generated by appending a specific peptide sequence termed ad2 (SEQ ID NO:11) to the C-terminus of CH1. To generate BP1-hFc×anti-VEGFR1Fab, BP1-hFc-ddd2 (Example 6) is mixed with the B-form of anti-VEGFR2 and reduced with TCEP for 1 h. Following removal of TCEP, DMSO is added to a final concentration of 10% to induce the formation of disulfide bonds between the ddd2 and ad2 present in each of the two parental proteins.

```
ad2
GGCGQIEYLAKQIVDNAIQQAGC      (SEQ ID NO: 11)
```

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the methods described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of identifying a PlGF ligand that inhibits angiogenesis, tumor growth or tumor metastasis comprising:

a) obtaining a phage display peptide library;

b) panning the library against human PlGF;

c) selecting at least one positive phage after panning;

d) sequencing at least one nucleic acid that encodes a peptide insert in the positive phage, wherein the peptide insert in the positive phage is a PlGF ligand; and e) assaying the PlGF ligand for inhibition of angiogenesis, tumor growth or tumor metastasis wherein the PlGF ligand binds to both PlGF and Flt-1 (Fms-like tyrosine kinase receptor).

2. The method of claim 1, wherein positive phage are selected after three rounds of panning.

3. The method of claim 1, wherein the tumor is a breast cancer.

4. The method of claim 1, wherein the PlGF ligand binds to the heparin binding sites on PlGF-2 and Flt-1.

5. The method of claim 1, wherein the PlGF ligand inhibits heparin binding to PlGF and/or Flt-1.

6. The method of claim 1, wherein heparin inhibits binding of the PlGF ligand to PlGF and/or Flt-1.

7. The method of claim 1, further comprising selecting at least one PlGF ligand that exhibits one or more characteristics selected from the group consisting of:

(i) binds to the heparin binding sites on PlGF-2 and Flt-1;

(ii) inhibits heparin binding to PlGF and/or Flt-1; and (iii) is inhibited from binding to PlGF and/or Flt-1 by heparin.

8. The method of claim 7, wherein the PlGF ligand exhibits each of the characteristics of:

(i) binds to the heparin binding sites on PlGF-2 and Flt-1;

(ii) inhibits heparin binding to PlGF and/or Flt-1; and (iii) is inhibited from binding to PlGF and/or Flt-1 by heparin.

9. The method of claim 8, wherein the PlGF ligand comprises the amino acid sequence of BP-1 (SEQ ID NO:1), BP-2 (SEQ ID NO:2), BP-3 (SEQ ID NO:3) or BP-4 (SEQ ID NO:4).

10. The method of claim 1, wherein the tumor is selected from the group consisting of a lymphoma, a leukemia, a myeloma, a sarcoma, a glioma, a melanoma and a carcinoma.

11. The method of claim 1, wherein the PlGF ligand inhibits angiogenesis, tumor growth or metastasis in at least one tumor selected from the group consisting of a lymphoma, a leukemia, a myeloma, a sarcoma, a glioma, a melanoma and a carcinoma.

12. The method of claim 1, wherein the tumor is selected from the group consisting of acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal cancer, gastric cancer, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer.

13. The method of claim 1, wherein the PlGF ligand inhibits cancer cell survival and/or motility.

* * * * *

SEQUENCE LISTING

```
<160> NUMBER OF SEQ ID NOS: 11

<210> SEQ ID NO 1
<211> LENGTH: 20
<212> TYPE: PRT
<213> ORGANISM: Homo sapiens

<400> SEQUENCE: 1

Ser His Arg Tyr Arg Leu Ala Ile Gln Leu His Ala Ser Asp Ser Ser
1               5                   10                  15

Ser Ser Cys Val
            20


<210> SEQ ID NO 2
<211> LENGTH: 9
<212> TYPE: PRT
<213> ORGANISM: Homo sapiens

<400> SEQUENCE: 2

Gln Asp Asp His Leu Thr Thr Gly Arg
1               5


<210> SEQ ID NO 3
<211> LENGTH: 12
<212> TYPE: PRT
<213> ORGANISM: Homo sapiens
```

<400> SEQUENCE: 3

Gln Glu Ala Phe Asn Arg Leu Thr Ser Arg Met His
1 5 10

<210> SEQ ID NO 4
<211> LENGTH: 12
<212> TYPE: PRT
<213> ORGANISM: Homo sapiens

<400> SEQUENCE: 4

Arg Met Pro Tyr Ser Glu His Ser Ala Pro Leu Gly
1 5 10

<210> SEQ ID NO 5
<211> LENGTH: 8
<212> TYPE: PRT
<213> ORGANISM: Artificial
<220> FEATURE:
<223> OTHER INFORMATION: Artificial Peptide, Synthetic

<400> SEQUENCE: 5

Asp Tyr Lys Asp Asp Asp Asp Lys
1 5

<210> SEQ ID NO 6
<211> LENGTH: 20
<212> TYPE: DNA
<213> ORGANISM: Artificial
<220> FEATURE:
<223> OTHER INFORMATION: Synthetic Oligonucleotides

<400> SEQUENCE: 6
tctagagcac acaggacctc 20

<210> SEQ ID NO 7
<211> LENGTH: 20
<212> TYPE: DNA
<213> ORGANISM: Artificial
<220> FEATURE:
<223> OTHER INFORMATION: Synthetic Oligonucleotides

<400> SEQUENCE: 7
gaagcttgga gtggacacct 20

<210> SEQ ID NO 8
<211> LENGTH: 20
<212> TYPE: DNA
<213> ORGANISM: Artificial
<220> FEATURE:
<223> OTHER INFORMATION: Synthetic Oligonucleotides

<400> SEQUENCE: 8
aagcttccga caaaactcac 20

<210> SEQ ID NO 9
<211> LENGTH: 20
<212> TYPE: DNA
<213> ORGANISM: Artificial
<220> FEATURE:
<223> OTHER INFORMATION: Synthetic Oligonucleotides

<400> SEQUENCE: 9
ccgcggcttt gtcttggcat 20

<210> SEQ ID NO 10
<211> LENGTH: 46

```
<212> TYPE: PRT
<213> ORGANISM: Artificial
<220> FEATURE:
<223> OTHER INFORMATION: Synthetic Peptide

<400> SEQUENCE: 10

Met Cys Gly His Ile Gln Ile Pro Pro Gly Leu Thr Glu Leu Leu Gln
1               5                   10                  15

Gly Tyr Thr Val Glu Val Leu Arg Gln Gln Pro Pro Asp Leu Val Glu
            20                  25                  30

Phe Ala Val Glu Tyr Phe Thr Arg Leu Arg Glu Ala Arg Ala
        35                  40                  45


<210> SEQ ID NO 11
<211> LENGTH: 23
<212> TYPE: PRT
<213> ORGANISM: Artificial
<220> FEATURE:
<223> OTHER INFORMATION: Synthetic peptide

<400> SEQUENCE: 11

Gly Gly Cys Gly Gln Ile Glu Tyr Leu Ala Lys Gln Ile Val Asp Asn
1               5                   10                  15

Ala Ile Gln Gln Ala Gly Cys
            20
```